(12) United States Patent
Debenham et al.

(10) Patent No.: US 9,139,871 B2
(45) Date of Patent: Sep. 22, 2015

(54) METHODS AND APPARATUSES

(75) Inventors: Paul Gerald Debenham, Middlesex (GB); John David Moore, Middlesex (GB)

(73) Assignee: LGC Limited (GB)

( * ) Notice: Subject to any disclaimer, the term of this patent is extended or adjusted under 35 U.S.C. 154(b) by 0 days.

(21) Appl. No.: 13/704,787

(22) PCT Filed: Jun. 17, 2011

(86) PCT No.: PCT/GB2011/051133
§ 371 (c)(1),
(2), (4) Date: Dec. 17, 2012

(87) PCT Pub. No.: WO2011/158037
PCT Pub. Date: Dec. 22, 2011

(65) Prior Publication Data
US 2013/0157315 A1 Jun. 20, 2013

(30) Foreign Application Priority Data

Jun. 18, 2010 (GB) .................................. 1010237.4

(51) Int. Cl.
*G01N 1/02* (2006.01)
*C12M 3/00* (2006.01)
*C12Q 1/68* (2006.01)
*G01N 1/00* (2006.01)

(52) U.S. Cl.
CPC .............. *C12Q 1/686* (2013.01); *C12Q 1/6806* (2013.01); *C12Q 1/6848* (2013.01); *G01N 1/02* (2013.01); *G01N 2001/007* (2013.01); *G01N 2001/028* (2013.01)

(58) Field of Classification Search
CPC ... C12Q 1/686; G01N 1/02; G01N 2001/007; G01N 2001/028; G01N 2001/2291
See application file for complete search history.

(56) References Cited

U.S. PATENT DOCUMENTS

| 6,103,192 | A | 8/2000 | Stapleton et al. |
| 2002/0110812 | A1 | 8/2002 | Naegele |
| 2003/0059345 | A1 | 3/2003 | Gilbert et al. |
| 2004/0152085 | A1 | 8/2004 | Terlesky et al. |
| 2008/0058676 | A1 | 3/2008 | Yong |
| 2013/0116596 | A1* | 5/2013 | Birnboim et al. ............. 600/570 |

FOREIGN PATENT DOCUMENTS

| JP | 2005-110687 | 4/2005 |
| WO | WO 9934214 A1 | 7/1999 |
| WO | WO 2005032377 A1 | 4/2005 |
| WO | WO 2008030820 A2 | 3/2008 |
| WO | WO 2009129397 A2 | 10/2009 |
| WO | WO 2010027283 A1 | 3/2010 |

OTHER PUBLICATIONS

Instruction sheet of Phusion Human Specimen Direct PCR Kit. Thermo Scientific (2010), retrieved from internet, http://www.thermoscientificbio.com/uploadedFiles/Resources/tech-manual-f-150-phusion-human-specimen-direct-pcr-kit.pdf, pp. 1-2.*
International Search Report and Written Opinion of the ISA/EPO for International Application PCT/GB2011/051133 mailed Feb. 8, 2012.
Barbany et al., "Molecular Genetic Applications of Streptavidin-Coded Manifold Supports," (1999) Biomolecular Engineering 16, 105-111.
Barbaro et al., "Detection of STRs from Body Fluid Collected on IsoCode Paper-Based Devices," (2004) Forensic Science International 146S, S127-S128.
Inouye & Hondo, "Microplate Hybridization of Amplified Viral DNA Segment," (1990) J. Clin. Microbiol. 28(6), 1469-1472.
Nikiforov & Rogers, "The Use of 96-Well Polystyrene Plates for DNA Hybridization-Based Assays: an Evaluation of Different Approaches to Oligonucleotide Immobilization," (1995) Analyt. Biochem. 227, 201-209.
Fang-Chin Wu et al., Genetic Polymorphisms of Y-Chromosomal Short Tandem Repeat Loci in Atayal Population of Taiwan, Croatian Medical Journal 2009 50:313-320.
Product Description for Phusion® Human Specimen Direct PCR Kit, publication XP055012357, online Jun. 14, 2010.

\* cited by examiner

*Primary Examiner* — Kenneth R. Horlick
*Assistant Examiner* — David Thomas
(74) *Attorney, Agent, or Firm* — Geoffrey M. Karny

(57) ABSTRACT

A method for amplifying nucleic acid from a higher eukaryotic, such as mammalian or plant, nucleic acid source, the method comprising (a) contacting a sampling device with the source of higher eukaryotic, such as mammalian or plant, nucleic acid such that following said contacting, higher eukaryotic such as mammalian or plant nucleic acid-containing material is adhered to at least part of the sampling device, wherein the sampling device, or part thereof to which the nucleic acid-containing material is adhered, is made of a suitable polymeric material; (b) introducing the sampling device or part thereof to which the nucleic acid-containing material is adhered into a reaction vessel which contains a reaction mixture for carrying out a nucleic acid amplification reaction, without any prior treatment of the nucleic acid-containing material; and (c) performing a nucleic acid amplification reaction.

25 Claims, 21 Drawing Sheets

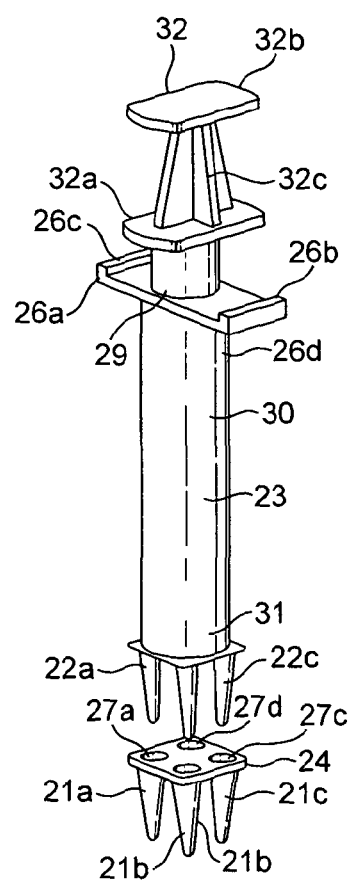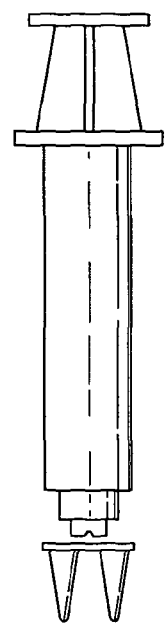
FIG. 11
FIG. 12

METHODS AND APPARATUSES

This application is a U.S. national phase application of, and claims the benefit of, International Patent Application No. PCT/GB2011/051133, filed Jun. 17, 2011, and it claims priority to foreign patent application GB 1010237.4, filed Jun. 18, 2010. The disclosure of these applications are expressly incorporated herein by reference in their entireties.

The present invention relates to methods and apparatuses for collecting nucleic acid samples for use in nucleic acid amplification reactions. The invention particularly relates to methods and apparatuses which are useful for collecting samples for forensic analysis, which may be used at eg. a crime or accident scene or a location at which biological contamination has occurred, and which are suitable for use with the minimum of manual intervention.

The listing or discussion of an apparently prior-published document in this specification should not necessarily be taken as acknowledgment that the document is part of the state of the art or is common general knowledge.

Presently, the standard laboratory preparation of mammalian (including human) DNA for analysis from solid biological samples requires some or all of the following:

The sample needs to be treated in some manner, through some form of wetting or application of a solution so as to remove the cells from the matrix it is present in, e.g. blood dried within a fabric, or skin cells on a cotton swab etc. In other words the sample transfer is achieved by liquid solubilisation.

The sample has to be treated in some way so as to facilitate the separation of the DNA from the cellular matrix of proteins, carbohydrates, other nucleic acids etc (ie a need to isolate DNA).

The separated DNA needs to be purged of binding proteins etc so as to enable the DNA analysis process to commence—e.g. access for DNA polymerases to copy DNA in a polymerase chain reaction (PCR), or access for enzymes in respect of other DNA amplification processes or restriction enzymes to bind and cleave the DNA sequence (ie a need to clean DNA).

The preparation needs to purge the sample of inhibitors, DNAses etc (ie a need to remove chemicals inhibitory of DNA analysis).

Dry samples need to be solvated to dissolve the cellular material into solution for any of the above reactions to proceed (ie a requirement for cells/DNA to be in solution).

The above processes require careful manipulation of the sample, measurement aliquots of preparative reagents etc all of which normally require a laboratory setting and trained personnel to undertake.

Hence, the general understanding is that mammalian (including human) cells need to be in solution for treatment and/or preparative manipulation, and need to be pre-treated to prepare them for DNA analysis.

Sampling cellular solutions directly into DNA analysis reactions is possible without need for preparative steps, although it involves limited sample types and/or specialised treatment to effect DNA analysis. It has been established that saliva can be placed directly, or diluted, into PCR reactions and the genomic DNA can be analysed. Placing blood directly, or diluted, into PCR reactions has been variously shown to require specialised buffers and enzymes in order to proceed with any degree of reproducible success. PCR inhibitors in cell solutions need to be addressed, often by dilution. Tissue culture cells need to be harvested from their culturing environment and need to be washed free of the media etc before being placed into a PCR reaction.

Cells in solution in other words normally are amenable to direct placement into PCR analysis equipment as long as appropriate dilution or polymerase enzymology is applied to optimise the analysis.

Glass surfaces and materials have long been established as a hydrophilic binding surface for cells and DNA and also a suitable surface to prime or contain a PCR reaction (for example, Nanassy et al Analytical Biochemistry 2007, vol 365 p 240-245 shows that genomic DNA was recovered efficiently from untreated glass slides (suitable for PCR)).

WO03/057910 relates to a method for the isolation of DNA using a material with an unmodified silica surface, and subsequent amplification in the presence of the unmodified silica. The examples all suggest that a lysis reaction is performed first to make the DNA available.

WO01/14590 describes a methodology using silica-containing magnetic beads placed within a DNA target mixture then separating the DNA bound to the silica matrix from the mixture using external magnetic forces. The examples indicate that DNA is made available to the silica through a prior cell lysis procedure.

No glass sampling device has been developed specifically to contact a sample, whether wet or dry, without prior preparative treatment to transfer the cells by contact directly from source into a PCR reaction. To date no sampling device has been made which utilises the known property of glass to collect and transfer cells/DNA by applying them to, for example, dry/solid surfaces so as to transfer them directly into a DNA/RNA amplification reaction.

The use of other solid surfaces to capture cells and DNA suitable for DNA/RNA amplification analysis has been investigated and it is known to provide microbial cultures in which bacterial colonies can be directly touched (e.g. with a wooden tooth pick) and bacterial cells transferred into PCR reactions without any treatment (for plasmids and genome).

Sticky surfaces, e.g. postage stamps, can bind cells when licked. The sticky material is not suitable for direct placement into PCR's and must first be treated to dissolve away the glue materials (e.g. by xylene pre-treatment of the stamps before DNA extraction occurs). EP 1 972 688 provides a method of amplifying a nucleic acid from a micro-organism involving a solid surface at low pH (3.00-6.00), washing the surface to remove unbound materials and then using the surface for PCR by successive steps within the same vessel. WO2006/036243 and WO2006/036246 teach the use of materials to bind cellular solutions such that the nucleic acid is suitable for subsequent release for analysis with subsequent treatment. Preferred solid phase support materials use a quaternary onium nucleic acid binding portion.

U.S. Pat. Nos. 5,496,562, 5,807,527, 6,27,226 and 6,645,717 relate to cellulose or glass fibre matrix which has been pre-soaked with chemicals to lyse cells such that if blood or saliva is put onto the surface it will be absorbed and simultaneously be preserved by the chemicals and dry down. The DNA-containing material has to be pre-treated to wash away the chemicals before being used in a PCR reaction.

Silicone (and Santoprene and other thermoplastic elastomer) surfaces have been traditionally considered as inert to the process of capturing DNA and providing surfaces that naturally retain DNA in a form suitable for PCR analysis. Silicone comes in many forms depending on the side groups attached to the silicon-oxygen backbone. Whilst it has been established that hydrophilic side groups such as hydroxyl groups create polymers that bind DNA, silicone is normally constituted with alkyl or aryl groups creating a hydrophobic source considered to be biologically inert.

IE20040589 indicates that silicone is used as an inert carrier fluid. JP2007244389 indicates that silicone is used as an inert layer in which grooves are cut to allow flow about the glass surface for PCR but to prevent leakage (i.e. silicone is presumed to be inert in the process). JP2008012434 indicates that silicone is a matrix into which DNA can be immobilised by use of an amphiphilic solution mixed with an organic solvent to get the DNA into the net structure of silicone where the DNA is then fixed by removing the solvent. This is not a natural absorbance process since amphiphilic solvents have hydrophilic and hydrophobic parts and so can be used to carry the hydrophilic parts and/or be used to carry the hydrophobic DNA into hydrophobic structures. The solvent is then removed to deposit the DNA thereby overcoming the assumed inhibition of absorbence of DNA. The presence of unpolymerised siloxane molecules within PDMS (Poly Di Methyl Siloxane) has been found to improve the use of PDMS as a stamp in the printing of solutions of DNA in microchip/fluidic devices (Thibault et al Langmuir 2007, 23, 10706-10714). The mechanism is not understood but the solvent extraction of unpolymerised siloxane reduces the (assumed) absorbance and transfer of DNA in the stamping process. No dry contact with a source of DNA has been explored previously.

Hence the foregoing patent applications and publications seem to be based on the premise that silicone and thermoplastic elastomers are inert materials with respect to binding cells/DNA but that the inert surface property can be modified to increase DNA adsorption from liquid contact with DNA solutions.

Plastic surfaces have historically been considered neutral to the process of capturing cells and providing a surface to enable PCR analysis. Plastics are essentially hydrophobic surfaces and are considered to require treatment to be appropriate to bind cells or DNA. As an example one may consider the treatment of plastic surfaces for cell adhesion for tissue culture. Polycarbonate surfaces are typically treated with strong UV, or ozone to create a hydrophilic surface. See Yanchao et al (2007) *Anal. Chem.* 79, 426-433 which describes different treatments of polystyrene, polycarbonate, polymethylmethacrylate and polypropylene to gain the most suitable binding. DNA probe attachment on plastic surfaces and microfluidic hybridisation array channel devices with sample oscillation are described in Liu & Rauch, *Analytical Biochemistry* 2003, vol 317, p 76-84. EP 0 389 063 teaches that polystyrene can be used to isolate nucleic acid from biological materials in the presence of chaotropic substances such as guanidinium salt, sodium iodide, potassium iodide, sodium isothiocyanate etc. Polypropylene is promoted as the material of choice for PCR reaction vessels as the material is highly inert (see studies by ABgene reported in INSights vol 13 2002 by Anne van der Valk). Binding is estimated for whole tube surfaces exposed to 200 ng human genomic DNA at less than 5 ng.

Thus, the paradigm is that untreated plastic is not a suitable surface for capturing cells or DNA without prior treatment.

EP 1 675 511 describes a swabbing device that is introduced into a chamber that by manipulation of the device brings the swab into contact with reagents and subsequently the test strip, but the device is not used for nucleic acid analysis. WO 2005/047451 relates to a spoon with a detachable end designed for collecting mouth cells and placing them in a stabilized solution in a tube. DNA is recovered from the cells for further analysis. US 2008/0131876 describes a method of amplifying nucleic acids from a cell sample by contacting it with a special solution that modifies the cells ready for PCR without requiring DNA extraction. WO 2008/006501 relates to a device that delivers a swab directly into a chamber linked to a microfluidic device to perform the PCR reaction. EP 1 049 801 mentions using a polymeric membrane that can be charged to bind DNA which can then be eluted. Nikiforov & Rogers (1995) *Anal. Biochem.* 227, 201-209 relates to the use of 96-well polystyrene plates for DNA hybridization-based assays. Inouye & Hondo (1990) *J. Clin. Microbiol.* 28, 1469-1472 relates to microplate hybridization of amplified viral DNA segments.

At present, crime scene samples are either swabbed (eg blood stain or fingerprint) or cut out from material (eg semen stain in underwear) and the swab or material placed into a cell lysis buffer from which DNA is subsequentially extracted (see, for example, Walsh et al (1991) *Biotechniques* 10, 506-513).

WO 2005/032377 describes a biological sampling kit comprising an anti-microbial agent and uses thereof.

US 2008/0058676 describes a segmented collector swab system.

WO 2010/027283 describes a sample collection device suitable for low-volume extraction.

WO 2009/129397 describes a high throughput dispenser.

US 2003/0059345 describes a two-pin liquid sampling device.

Barbany et al (1999) *Biomolecular Engineering* 16, 105-111 describe molecular genetic applications of streptavidin-coated manifold supports.

WO 99/34214 describes solid-phase tips and uses relating thereto.

US 2002/0110812 describes a nucleic acid collection barrier method and apparatus.

U.S. Pat. No. 6,103,192 describes immobilizing and processing specimens on matrix materials for the identification of nucleic acid sequences.

Barbaro et al (2004) *Forensic Science International* 146S, S127-S128 describes the detection of STRs from body fluid collected on IsoCode paper-based devices.

US 2004/0152085 describes a surface for collection and/or purification of nucleic acids.

There remains the need for methods and devices which are useful for collecting nucleic acid-containing samples for forensic analysis, which may be used at the scene of a crime, accident or other event, and which are suitable for use with the minimum of manual intervention in a "contact and go" or "collect and go" approach.

The present invention provides, amongst other things, methods and devices requiring only contact of a sample (solid or liquid) both to capture and to present the nucleic acid (typically mammalian DNA) in a form suitable for DNA amplification (PCR or other) when subsequently placed within the amplification reagents. The presence of the device or a part thereof within the reagents does not interfere with the amplification process nor the subsequent analytical (e.g. fluorescence) detection process.

The work described herein demonstrates that the direct capture and delivery of mammalian (including human) cells for nucleic acid amplification analysis can be achieved in a single step just by contact transfer ("contact and go" or "collect and go") by certain polymer surfaces including plastic, silicone and glass, that wetting, or solvation, of the target cells is not required for their capture or transfer into the nucleic acid amplification reaction, that certain simple conventional plastic and/or silicone surfaces are sufficient (typically without modification, although treatments which "DNA sterilize" the polymer may be used, such as UV irradiation or ethylene oxide gas treatment) to act as or as part of a sampling device to transfer cells from a wet or dry cellular surface or stain, that the property of capturing of the cells on the surface is such that the DNA is suitable for PCR analysis and remains bound and reusable to be placed into a second PCR reaction if required, and that the polymer sampling devices, or at least a part thereof, can be left within the amplification reaction without any detriment to the reaction.

The work described herein further provides devices such that cells on a surface can be contacted and transferred not only into a single DNA analysis reaction, but also into multiple discrete simultaneous reactions if required.

The invention establishes that, contrary to the dogma that plastics, silicones and thermoplastic elastomers have to be specially treated to bind nucleic acid otherwise they are unsuitable for capturing mammalian (including human) samples and priming amplification reactions directly, certain plastic and silicone surfaces can act as a sampling device suitable to prime a nucleic acid amplifying reaction simply by placing the sample directly in contact with the surface, and then depositing the contact surface into the DNA analysis reaction. These surfaces may be untreated or they may be treated to "DNA sterilize" them, so that they do not have associated therewith any detectable nucleic acid which would interfere with a nucleic acid amplification and detection reaction, as is described in more detail below. Other native surfaces, such as wood, latex and metals, were tried out as direct sampling devices and were found not to be suitable.

The methods and devices described herein provide portability, ease of use and analysis within a short space of time, and at the site that the nucleic acid sample is taken.

A first aspect of the invention provides a method for preparing a reaction vessel which contains a reaction mixture and nucleic acid-containing material and is ready to carry out a nucleic acid amplification reaction, the method comprising
(a) providing a reaction vessel with a single chamber which contains the reaction mixture for carrying out a nucleic acid amplification reaction and which reaction vessel is sealed;
(b) providing a sampling device;
(c) contacting the sampling device with the nucleic acid-containing material such that following said contacting nucleic acid-containing material is adhered to at least part of the sampling device;
(d) unsealing the reaction vessel;
(e) placing the sampling device, or part thereof to which the nucleic acid-containing material is adhered, into the reaction vessel so that the nucleic-acid containing material is in contact with the reaction mixture;
(f) resealing the reaction vessel to be airtight, with the sampling device, or part thereof to which the nucleic acid-containing material is adhered, still present in the reaction vessel.

The reaction vessel may be any suitable reaction vessel in which to carry out a nucleic acid amplification reaction. Typically, the reaction vessel is made from plastic, in particular polypropylene. Conveniently, the reaction vessel has a volume of from 50 µl to 3 ml, preferably from 100 µl to 1.5 ml. Typically, the reaction vessel has a circular cross-section of from 3 mm to 10 mm, typically around 5 mm.

Although the method may be carried out using a single reaction vessel, it is convenient for a plurality of reaction vessels to be joined together or supported in a common support, and for them to be prepared simultaneously. Thus, typically, two or three or four or six or eight or ten reaction vessels are joined together to form a regular array. Each reaction vessel may contain the same reaction mixture (for example, the same PCR reaction mixture to allow for amplification and detection of the same genetic locus or loci), or they may contain different reaction mixtures (for example, different PCR reaction mixtures to allow for amplification and detection of different genetic loci). The regular arrays of reaction vessels are conveniently configured to engage with a suitable instrument for carrying out the nucleic acid amplification reaction and/or detection of products. Suitable instruments include thermocycler instruments and fluorescent detection instruments. In some embodiments, the array of reaction vessels may contain a reaction vessel that already contains known and predetermined nucleic acid-containing material as a control.

Nucleic acid-containing material is placed into the reaction vessels using the sampling device such that the sampling device, or part thereof to which the nucleic acid-containing material is adhered, is present in the reaction vessel. Typically, the nucleic acid-containing material is retained on the sampling device or part thereof, and this is submerged within the reaction mixture. During a nucleic acid amplification reaction, amplified copies of the DNA are released into the reaction mixture solution.

When there is a plurality of reaction vessels joined together as discussed, typically the sampling device, or part thereof to which the nucleic acid-containing material is adhered, is configured to allow for the nucleic acid-containing material to be distributed between the plurality of reaction vessels. Thus, for example, when there are N reaction vessels, the sampling device conveniently is configured such that it allows for the nucleic acid-containing material to be distributed into each of the N reaction vessels. Preferably the material is distributed substantially evenly between the reaction vessels. Typically, N may be 2, 3, 4, 6 or 8. Preferably, N is 4. Preferably, when N is 4, the reaction vessels are located at the corners of a square.

It will be appreciated that the reaction vessel provided in step (a) is sealed. Typically the seal is air-tight. This means that the reaction mixture can be kept free from contamination until use. In use the seal is broken prior to step (e), but it will be appreciated that steps (c) and (d) may be carried out in any order. The seal may be any suitable seal, and conveniently may readily be removed. A typical seal for use with the reaction vessel is foil or a plastic film which may be pulled off. Other seals, such as in the form of push-in stoppers, are also contemplated for the reaction vessel provided in step (a). In step (f), the resealing of the reaction vessel prevents evaporation or spillage during the subsequent analytical procedures. The nucleic acid-containing material generally remains in contact with the reaction mixture.

The sampling device has several important features. Upon contact with the nucleic acid-containing material, sufficient of the material adheres to the sampling device to allow for nucleic acid amplification when it, or the part thereof to which the nucleic acid-containing material is adhered, is placed in the reaction vessel and a nucleic acid amplification reaction is performed. Conveniently the sampling device, or at least part thereof to which the nucleic acid-containing material is adhered, is therefore able to bind cellular material, particularly mammalian cellular material which is present in a dried sample as is described in more detail below. By "adhered" we include the meaning that nucleic acid-containing material becomes attached to the sampling device or part thereof directly without any requirement for a separate adhesive material. This is achieved by contacting the sampling device or part thereof with the nucleic-acid containing material, for example by rubbing the device or part thereof on the material. The sampling device or part thereof is typically non-porous.

The sampling device, or the part thereof to which the nucleic acid-containing material is adhered, remains in the reaction vessel during the nucleic acid amplification reaction, and therefore must be compatible with the conditions of the nucleic acid amplification reaction.

Surprisingly, it has been found that the following polymers, without any chemical derivatization or pre-treatment, are able to collect sufficient nucleic acid-containing material upon contact with a sample, and do not interfere with a nucleic acid amplification reaction when present during the reaction. Furthermore, surprisingly, it has been found that following the nucleic acid amplification reaction, sufficient nucleic acid-containing material remains associated with these polymers that it can be used in a further nucleic acid amplification reaction. The sample may be a wet or a dry sample. A wet sample may adhere to the device or part thereof by liquid adhesion and transfer. Typically, when the sample is a dry sample, there is adhesion of cellular material that contains nucleic acid. Preferably, the sample is a dry sample.

The polymers are glass, Cyclic olefin copolymer such as Topas, Acrylic such as polymethylmethacrylate (PMMA), Crystal Polystyrene, Polypropylene, high-density polyethylene (HDPE), Polycarbonate, Medium impact Polystyrene, polyvinylchloride (PVC), Liquid Crystal Polymer 30%, Trans acrylonitrile-butadiene-styrene (Trans ABS), Acetal copolymer, Polyester, Polyetherimide, Polyethylene, Nylon, Polyether Polyurethane, Styrene Butadiene block copolymer, Polypropylene random copolymer, Ethylene-vinyl acetate, siloxane, such as polymethyl dioxene siloxane (PDMS), and thermoplastic elastomer such as santoprene. Preferably, the polymer is one to which a dry nucleic acid-containing material, such as a dry sample of cellular material, is able to adhere upon contact between the device or part thereof made from the polymer and the sample. Thus, it is particularly preferred that the sampling device, or at least the part thereof to which the nucleic acid-containing material is adhered, is made from one or more of these polymers. It is preferred that the polymer is not in the form of a foam, particularly a loose foam. The polymer is not latex. The polymer may be any suitable polymer impregnated with glass, such as any of the above-listed polymers (except glass) impregnated with glass. Typically, the polymer withstands a temperature of 100° C. For example, it does not decompose or deform at this temperature.

It is particularly preferred if the polymer is any of PMMA, polypropylene, polycarbonate and PDMS. Polycarbonate is especially preferred.

A number of different designs of sampling device, some of which are described in more detail below, are suitable for use in the invention. They fall into two general categories including, firstly, those in which the sampling device, or part thereof to which the nucleic acid-containing material is adhered, fits into the reaction vessel (after it has been unsealed) and allows for the reaction vessel to be resealed with a separate seal in step (f). The separate seal may be, for example, foil, a plastic film or a push-in stopper. The second, preferred, category is wherein the sampling device, or part thereof to which the nucleic acid-containing material is adhered, provides the seal that seals the reaction vessel in step (f). Embodiments of this category are described in more detail below.

Conveniently, the sampling device, or part thereof to which the nucleic acid-containing material is adhered, is placed directly into the reaction vessel with no additional treatment following sampling.

The reaction mixture is for carrying out any suitable nucleic acid amplification reaction including but not limited to polymerase chain reaction (PCR), or isothermal methods such as ligase chain reaction (LCR), loop-mediated isothermal amplification (LAMP) transcription mediated amplification (TMA), signal mediated amplification of RNA technology (SMART), strand displacement amplification (SDA) rolling circle amplification (RCA), isothermal multiple displacement amplification (IMDA), helicase dependent amplification (HAD), single primer isothermal amplification (SPIA), circular helicase dependent amplification (CDHA) and nucleic acid sequence-based amplification (NASBA). PCR is preferred; however it can be seen from the Examples that high-temperature treatment (close to 100° C.) is not required to make DNA available for amplification, and so lower-temperature methods such as LAMP, which is isothermal, are suitable.

Thus, the reaction mixture contains all of the necessary ingredients, except the nucleic acid to be analysed, for carrying out the nucleic acid amplification reaction.

Thus, for example, for a PCR, the reaction mixture contains PCR primers, deoxynucleotides, a DNA polymerase $Mg^{2+}$ ions and a buffered solution around pH7-8. For other nucleic acid amplification methods, other enzymes such as RNAse H or ligase are present.

It has been found that it is not necessary to pre-treat the nucleic acid-containing material prior to the nucleic acid amplification reaction. In addition, it may not be necessary to have any special reagents in the nucleic acid amplification reaction mixture, beyond those required for the reaction. Thus, it is preferred that the reaction mixture is substantially free of chaotropic agents. Similarly, it is preferred that the reaction mixture is substantially free of cell-lytic agents. However, in some embodiments non-ionic detergent, such as Tween-20, may be present. By "substantially free" of the said agents we mean that the agent is absent, or that it is present at such a low concentration as not to exert its chaotropic or cell-lytic effect, as the case may be. It is particularly preferred if the reaction mixture is substantially free of any of urea, guanidine salts (such as guanidine hydrochloride), detergent, especially ionic detergent.

In a particularly preferred embodiment, the reaction mixture also contains reagents for the detection of the nucleic acid product of the nucleic acid amplification reaction. Thus, typically, the reaction mixture also contains detectably-labelled nucleic acid probes. Particularly preferred probes are fluorescently-labelled oligonucleotide probes that are able to hybridise to the product of the nucleic acid amplification reaction. Suitable oligonucleotide probes and fluorescent detection systems are described in, for example WO 2001/73118, WO 2007/010268, WO2009/053679, all of which are incorporated herein by reference. It is particularly preferred that short tandem repeat (STR) analysis is performed, for example in human DNA fingerprinting. It will be appreciated that it is advantageous that the detection can be performed, during or following the nucleic amplification reaction, in the sealed reaction vessel since unsealing the vessel has the potential for the introduction of contamination. The results of the amplification may be observed directly in the reaction vessel, for example by light fluorescence, or by sampling from the reaction mixture solution, leaving the sampling device in the vessel, and analysing the amplified DNA, for example by gel electrophoresis.

The nucleic acid-containing material may be of any origin, but preferably is of higher eukaryotic, such as mammalian or plant, origin. Higher eukaryotes include animals, including vertebrates. Nucleic acid of mammalian, such as human, origin is preferred. It is preferred that the nucleic acid is DNA. It is preferred that the nucleic acid is genomic DNA, but viral nucleic acid, which is derived from a higher eukaryotic cell, is included in the term "of higher eukaryotic origin". Typically, the nucleic acid is present within mammalian cells, and the nucleic acid-containing material is mammalian cellular material. Mammalian, including human, cellular material includes blood, saliva, semen, cells such as skin cells and cellular material which is deposited on a solid surface, for example skin cells which may be left as part of a fingerprint. The nucleic acid-containing material may be substantially free of non-nucleic acid material.

For many applications, the nucleic acid-containing material is substantially dry. By "substantially dry" we mean that the sample has no visible signs of moisture associated with it. For example, the nucleic acid-containing material may be cells such as skin cells, dried blood, dried semen, dried saliva or other dried body fluids. Surprisingly it has been found to be unnecessary to solvate the dried material before taking a sample, and it has been found that the dried sample may be placed directly into the reaction vessel without prior treatment.

Although not limited to this use, it will readily be appreciated that the invention has applications in forensic science, particularly at the scene of crime. Clinical applications, such as genetic disease testing, and "source or origin" testing of food, plant and animal materials, and so on are also envisaged. Similarly the methods and apparatuses of the invention embrace within their scope nucleic acid sampling of eg. a site of disease contamination. As examples one may consider locations at which contamination by virulent disease pathogens (such as those for Avian Influenza, severe acute respiratory syndrome (SARS), so-called "Swine Flu" and Foot and Mouth Disease) has occurred. At such locations it can be extremely important to identify on a rapid basis the strain of the disease that has caused the contamination.

A second aspect of the invention provides a method for amplifying nucleic acid, the method comprising preparing a reaction vessel according to the first aspect of the invention, and performing a nucleic acid amplification reaction in the reaction vessel. Once the reaction vessel has been prepared, and therefore contains the reaction mixture containing the reagents for carrying out the nucleic acid amplification reaction and also contains the nucleic acid-containing material, the nucleic acid amplification reaction is performed in the usual way according to the type of reaction. Thus, for example, PCR may be carried out in a suitable thermocycler machine.

As noted above, surprisingly, it has been found that it is possible to reuse the sampling device, or at least the part thereof to which the nucleic acid acid-containing material is adhered, in a further nucleic acid amplification reaction since enough of the material is retained for at least a further nucleic acid amplification reaction. Thus, a third aspect of the invention provides a method for amplifying nucleic acid, the method comprising carrying out the method of the first aspect of the invention, removing the sampling device (or part thereof to which the nucleic acid-containing material is adhered) and placing it into a further reaction vessel, and performing a nucleic acid amplification reaction in the further reaction vessel. In one embodiment of the third aspect of the invention, the sampling device is removed and, if necessary, subjected to washes with a solution to remove any of the first reaction mixture before placing it into the further reaction vessel. It may not be necessary to subject the sampling device to washes if a different probe detecting the new target sequence is labelled with a different colour fluorophore since any remnant of the first reaction would be "invisible" to the subsequent analysis.

In another embodiment of the second aspect of the invention, the reaction mixture is removed from the reaction vessel after a first amplification reaction has been performed, the sampling device or part thereof is washed in situ in the reaction vessel, and then a second reaction mixture is added to the reaction vessel. In a further embodiment, the sampling device, or part thereof, may contain magnetic material, and retention in the reaction vessel can be achieved by applying an appropriate magnetic field.

Typically, the further reaction vessel is prepared essentially as is described in the first aspect of the invention. Although, generally, it may not be necessary to carry out a further nucleic acid amplification reaction, the invention allows for this and it may be of particular use where a further, corroborative or independent, nucleic acid amplification reaction is performed. This may be some time after the first nucleic acid amplification reaction.

A fourth aspect of the invention provides a method for amplifying nucleic acid from a higher eukaryotic such as mammalian or plant nucleic acid source, the method comprising
  (a) contacting a sampling device with the source of higher eukaryotic such as mammalian or plant nucleic acid such that following said contacting, higher eukaryotic such as mammalian or plant nucleic acid-containing material is adhered to at least part of the sampling device, wherein the sampling device, or part thereof to which the nucleic acid-containing material is adhered, is made of any of a suitable polymeric material;
  (b) introducing the sampling device or part thereof to which the nucleic acid-containing material is adhered into a reaction vessel which contains a reaction mixture for carrying out a nucleic acid amplification reaction, without any prior treatment of the nucleic acid-containing material; and
  (c) performing a nucleic acid amplification reaction.

The polymeric material is one to which a nucleic acid-containing material is adhered following contacting with the source of nucleic acid, for example by rubbing. The polymeric material is also one which does not prevent or substantially interfere with a nucleic acid amplification reaction when the polymeric material is present in the reaction mixture. Whether or not a polymer is a suitable polymer can be determined, for example as is described in the examples. In particular the protocol described in Example 2 may be used to determine suitability of the polymer, or the protocol of Example 11 may be used but in which PMMA is replaced by another polymer whose suitability is being tested, and the D16 probe is used.

Preferably the polymeric material is any of glass, Cyclic olefin copolymer such as Topas, Acrylic such as PMMA, Crystal Polystyrene, Polypropylene, HDPE, Polycarbonate, Medium impact Polystyrene, PVC, Liquid Crystal Polymer 30%, Trans ABS, Acetal copolymer, Polyester, Polyetherimide, Polyethylene, Nylon, Polyether Polyurethane, Styrene Butadiene block copolymer, Polypropylene random copolymer, Ethylene-vinyl acetate siloxane such as PDMS, and thermoplastic elastomer, such as Santoprene Conveniently, the higher eukaryotic such as mammalian or plant nucleic acid source is substantially dry as is discussed above. Conveniently the sampling device, or part thereof to which the nucleic acid-containing material is adhered, remains in the reaction vessel during step (c).

A fifth aspect of the invention provides a method for amplifying nucleic acid from a higher eukaryotic such as mammalian or plant nucleic acid source, the method comprising
  (a) contacting a sampling device with the source of higher eukaryotic such as mammalian or plant nucleic acid such that, following said contacting, higher eukaryotic such as mammalian or plant nucleic acid-containing material is adhered to at least part of the sampling device; wherein the source of higher eukaryotic such as mammalian or plant nucleic acid is substantially dry;

(b) introducing the sampling device, or part thereof to which the nucleic acid-containing material is adhered, into a reaction vessel which contains a reaction mixture for carrying out a nucleic acid amplification reaction without any prior treatment of the nucleic acid-containing material; and (c) performing a nucleic acid amplification reaction.

Conveniently, the sampling device or part thereof to which the nucleic acid-containing material is adhered is made of any of glass, Cyclic olefin copolymer such as Topas, Acrylic such as PMMA, Crystal Polystyrene, Polypropylene, HDPE, Polycarbonate, Medium impact Polystyrene, PVC, Liquid Crystal Polymer 30%, Trans ABS, Acetal copolymer, Polyester, Polyetherimide, Polyethylene, Nylon, Polyether Polyurethane, Styrene Butadiene block copolymer, Polypropylene random copolymer, Ethylene-vinyl acetate siloxane, such as PDMS, and thermoplastic elastomer such as Santoprene.

Conveniently the sampling device, or part thereof to which the nucleic acid-containing material is adhered, remains in the reaction vessel during step (c).

Typically, the reaction mixture in the fourth or fifth aspects of the invention is substantially free of chaotropic agents and/or is substantially free of cell-lytic agents (see the discussion above with respect to the first aspect of the invention).

A sixth aspect of the invention provides a method of preparing a data carrier which records the genotype associated with the nucleic acid from a nucleic acid-containing material, the method comprising carrying out the method of the second, fourth or fifth aspects of the invention, determining the genotype of the nucleic acid in the nucleic acid-containing material and recording the genotype on the data carrier. The genotype may be related to a SNP (single nucleotide polymorphism) or it may be related to a STR (short tandem repeat). The genotype may be a "DNA fingerprint". The data carrier may be any data carrier, but typically is an electronic data carrier such as a computer disk or flash memory. It will be appreciated that the data carrier, and the data thereon, may be used to compare the genotype of the nucleic acid from the sample analysed, with the genotype from other samples, or with a genotype stored in a database. This is especially useful for crime detection and law enforcement embodiments of the invention.

A seventh aspect of the invention provides the use of a nucleic acid sampling device to obtain nucleic acid from a higher eukaryotic, such as mammalian or plant nucleic acid, source and then to introduce the higher eukaryotic such as mammalian or plant nucleic acid source into a reaction vessel containing a nucleic acid amplification reaction mixture without prior treatment, wherein the source of higher eukaryotic such as mammalian or plant nucleic acid is substantially dry. Preferably nucleic acid is adherent to the sampling device or part thereof, the sampling device or part thereof to which the nucleic acid-containing material is adhered being made of any of glass, Cyclic olefin copolymer such as Topas, Acrylic such as PMMA, Crystal Polystyrene, Polypropylene, HDPE, Polycarbonate, Medium impact Polystyrene, PVC, Liquid Crystal Polymer 30%, Trans ABS, Acetal copolymer, Polyester, Polyetherimide, Polyethylene, Nylon, Polyether to Polyurethane, Styrene Butadiene block copolymer, Polypropylene random copolymer, Ethylene-vinyl acetate, siloxane such as PDMS, and thermoplastic elastomer such as Santoprene. Conveniently, the nucleic acid sampling device or part thereof to which the nucleic acid-containing material is adhered remains in the reaction vessel during the nucleic acid amplification reaction.

An eighth aspect of the invention provides a kit comprising (a) a reaction vessel which contains a reaction mixture for carrying out a nucleic acid amplification reaction, which reaction vessel is sealed and (b) a sampling device to at least part of which nucleic acid-containing material can be adhered following contact with said material, wherein the sampling device, or part thereof to which the nucleic acid-containing material is adhered, can be introduced into the reaction vessel and a nucleic acid amplification reaction can be performed in the vessel in the presence of the sampling device, or part thereof to which the nucleic acid-containing material is adhered. The reaction vessel, reaction mixture, sampling device, nucleic acid-containing material and so on may be any as described with respect to earlier aspects of the invention. The preferences for these features are the same in this aspect of the invention.

Typically, the kit contains a plurality of reaction vessels which are joined together as is discussed above in the context of the first aspect of the invention. Typically, the sampling device, or part thereof to which the nucleic acid-containing material can be adhered, is configured to allow for the nucleic acid-containing material to be distributed between a plurality of reaction vessels as is discussed above in the context of the first aspect of the invention.

Conveniently, in some embodiments, the sampling device, or part thereof to which the nucleic acid-containing material can be adhered, provides a seal of the reaction vessel once the original seal is removed. Preferably, the sampling device, or part thereof to which the nucleic acid-containing material can be adhered, is made of any of glass, Cyclic olefin copolymer such as Topas, Acrylic such as PMMA, Crystal Polystyrene, Polypropylene, HDPE, Polycarbonate, Medium impact Polystyrene, PVC, Liquid Crystal Polymer 30%, Trans ABS, Acetal copolymer, Polyester, Polyetherimide, Polyethylene, Nylon, Polyether Polyurethane, Styrene Butadiene block copolymer, Polypropylene random copolymer, Ethylene-vinyl acetate siloxane, such as PDMS, and thermoplastic elastomer, such as Santoprene. Conveniently, the reaction mixture present in the reaction vessel is any reaction mixture as described above with respect to the earlier aspects of the invention.

According to a ninth aspect of the invention there is provided a nucleic acid sampling apparatus comprising at least one probe for supporting a nucleic acid sample; and a manipulator that is attachable to the probe such as to permit manoeuvring of the probe, the probe being separable from the manipulator.

Optionally the apparatus includes a receptacle, including a sealable opening, for containing one or more reagents and a nucleic acid sample, operation of the manipulator causing or permitting insertion of the probe via the opening so as to locate the sample in the receptacle; and the probe including a closure that on location of the sample in the receptacle closes the receptacle against engress or ingress of nucleic acid-containing material.

Further optional aspects of the apparatus of the invention are defined in the dependent claims. In particular in an optional arrangement within the scope of the invention the apparatus includes a receptacle including a sealable opening, for containing one or more reagents and a nucleic acid sample, operation of the manipulator causing or permitting insertion of the probe via the opening so as to locate the sample in the receptacle.

The invention will be described in more detail by reference to the following non-limiting Examples, embodiments and figures. In the figures:

FIG. 1 shows the peak heights obtained from SGMPlus (Applied Biosystems) analysis of a range of plastic "beads" used to transfer buccal cells and DNA from mouth-swabs. The plastic beads, analysed in triplicate, were 1) Topas, 2) Acrylic, 3) Crystal Polystyrene, 4) Polypropylene, 5) HDPE, 6) Polycarbonate, 7) Medium impact Polystyrene, 8) PVC, 9) Polyethylene-block-polyethylene glycol, 10) Poly(ethylene-co-acrylic acid), 11) Poly(Vinyl-alcohol-co-ethylene, 12) Poly(Ethylene-co-vinyl-acetate) graft maleic anhydride, 13) Liquid Crystal Polymer 30%, 14) Trans ABS, 15) Cyclic Olefin Copolymer, Topas 16) Acetal copolymer, 17) Polyester, 18) Polyetherimide, 19) Polyethylene, 20) Nylon, 21) Polyether Polyurethane, 22) Styrene Butadiene block copolymer, 23) Polypropylene random copolymer and 24) Ethylene-vinyl acetate.

FIG. 2 shows the number of peaks generated through SGMPlus analysis of a range of plastic "beads" used to transfer buccal cells and DNA from mouth-swabs. The plastic beads, analysed in triplicate, were 1) Topas, 2) Acrylic, 3) Crystal Polystyrene, 4) Polypropylene, 5) HDPE, 6) Polycarbonate, 7) Medium impact Polystyrene, 8) PVC, 9) Polyethylene-block-polyethylene glycol, 10) Poly(ethylene-co-acrylic acid), 11) Poly(Vinyl-alcohol-co-ethylene), 12) Poly(Ethylene-co-vinyl-acetate) graft maleic anhydride, 13) Liquid Crystal Polymer 30%, 14) Trans ABS, 15) Cyclic Olefin Copolymer, 16) Acetal copolymer, 17) Polyester, 18) Polyetherimide, 19) Polyethylene, 20) Nylon, 21) Polyether Polyurethane, 22) Styrene Butadiene block copolymer, 23) Polypropylene random copolymer and 24) Ethylene-vinyl acetate. 21 DNA products should be generated if all targets are successfully amplified.

FIG. 3 illustrates melting peak data generated with the D16S539 HyBeacon test, A) Results from PMMA using a rubbing method to sample blood on fabric and saliva on glass by contact. B) Results from PDMS using a rubbing method to sample blood on fabric, blood on glass, saliva on fabric and Saliva on glass. C) Results from Santoprene (8281-75MED) again using a rubbing action to sample blood on fabric, blood on glass, saliva on fabric and saliva on glass.

FIG. 4 shows melting peaks obtained from the D16S539 HyBeacon test, A) Results from PMMA in presence of extracted DNA. B) Results from PDMS in presence of extracted DNA. C) Results from Santoprene (8281-75MED) in presence of extracted DNA. Extracted DNA controls represented by darker traces.

FIG. 5 shows melting peaks obtained from the D16S539 test, A) Results from PMMA in presence of expressed buccal swab. B) Results from PDMS in presence of expressed buccal swab. C) Results from Santoprene (8281-75MED) in presence of expressed buccal swab. Expressed swab controls are represented by darker traces.

FIG. 6 shows i) Melting peaks obtained from the D16S539 test. A) Results from PMMA using a rubbing method to sample saliva on glass. B) Results from PDMS used to sample saliva on glass. C) Results from Santoprene (8281-75MED) used to sample saliva on glass FIG. 7 shows melting peaks obtained from the D18S51 HyBeacon test. Sampling surfaces were removed from the D16S539 test, gently washed, placed into D18S51 reactions and amplified. A) Results from PMMA using a rubbing method to sample saliva on glass. B) Results from PDMS used to sample saliva on glass. C) Results from Santoprene (8281-75MED) rubbed on saliva on glass.

FIGS. 11 to 16 show in perspective view the parts of another embodiment of apparatus in accordance with the invention.

Figure 1:
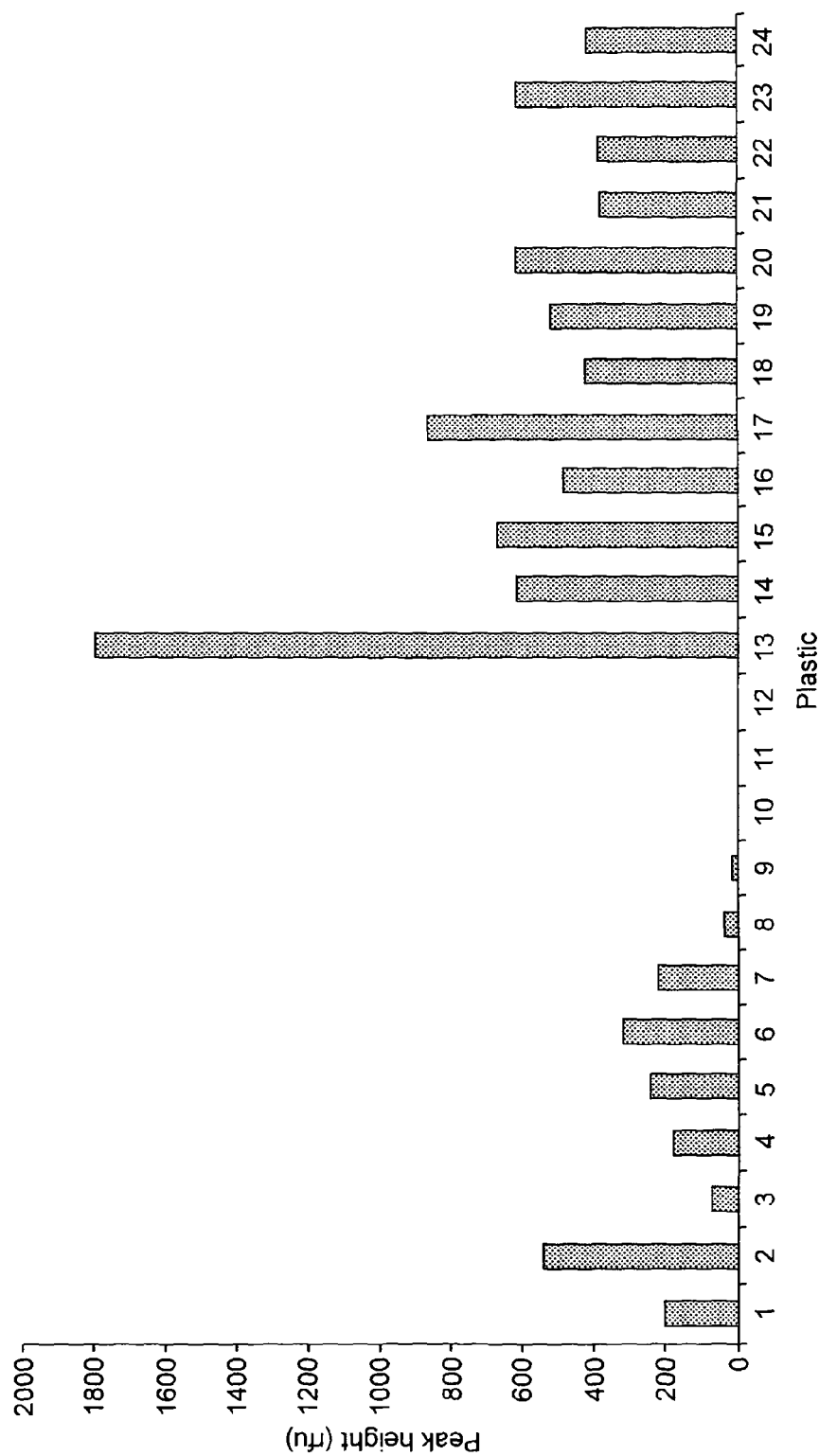

In this specification certain terms are used interchangeably in order to indicate the broad applicability of the principles of the invention. The following concordance table summarises the terms having equivalent meanings:

| Term 1 | Term 2 (Equivalent) |
|---|---|
| Reaction vessel | Receptacle |
| Nucleic acid-containing material | Nucleic acid sample |
| Sampling device | Sampling apparatus |

Moreover the terms "seal" and "sealing member" are used generally interchangeably herein, as the context permits.

Example 1

Materials and Methods Pertaining to the Further Examples

Bead Production

Plastic granules were collected from plastic suppliers (Sovereign; Slough, Matrix Plastics; Slough, EuroPlaz; Southminster) for the following plastics; 1) Topas, 2) Acrylic, 3) Crystal Polystyrene, 4) Polypropylene, 5) HDPE, 6) Polycarbonate, 7) Medium impact Polystyrene, 8) PVC, 9) Polyethylene-block-polyethylene glycol, 10) Poly(ethylene-co-acrylic acid), 11) Poly(Vinyl-alcohol-co-ethylene) and 12) Poly(Ethylene-co-vinyl-acetate) graft maleic anhydride, 13) Liquid Crystal Polymer 30%, 14) Trans ABS, 15) Cyclic Olefin Copolymer, 16) Acetal copolymer, 17) Polyester, 18) Polyetherimide, 19) Polyethylene, 20) Nylon, 21) Polyether Polyurethane, 22) Styrene Butadiene block copolymer, 23)

Polypropylene random copolymer and 24) Ethylene-vinyl acetate. These were used in an unmodified manner and in later experiments cut with a scalpel to produce similar sized shards of plastic that were approximately 1.5 mm$^3$ in size. All plastics were irradiated with UV radiation at 257 nm to remove possible contaminating DNA. A brief description of the plastics is provided in Table 1.

AmpflSTR© SGMplus™ Summary

Amplification and interrogation of the STR targets was carried out with an AmpflSTR© SGMplus™ kit (Applied Biosystems). The AmpflSTR© SGMplus™ kit contains ten STRs (D16S539, D18S51, D19S433, D2S1338, D21S11, D3S1358, D8S1179, FGA, TH01 and vWA) and the Amelogenin sex test. The AmpflSTR© SGMplus™ kit was used as

TABLE 1

Summary of the properties of the plastics used.

| Plastic | Colour | Hardness | Approximate Size | Shape |
|---|---|---|---|---|
| Topas | Clear | Very Hard | H = 3 mm, r = 1 mm | Cylindrical |
| Acrylic | Clear | Very Hard | H = 3 mm, r = 2 mm | Cylindrical |
| Crystal polystyrene | Clear | Very Hard | H = 3 mm, r = 1 mm | Cylindrical |
| Polypropylene | Opaque Black | Hard | H = 3 mm, r = 1 mm | Cylindrical |
| HDPE | Opaque White | Very Hard | H = 2 mm, r = 1.5 mm | Convex Disc |
| Polycarbonate | Clear | Very Hard | H = 3 mm, r = 1 mm | Cylindrical |
| Medium impact polystyrene | Opaque White | Very Hard | H = 3 mm, r = 1 mm | Cylindrical |
| PVC | Clear | Medium to soft hardness almost flexible. | H = 2 mm, r = 1.5 mm | Convex Disc |
| Polythylene-block-polyethylene glycol | Semi-opaque white | Very soft wax like material. (Dissolved in reaction mix) | Approximately 1.5 mm$^3$ piece used | Irregular Shape |
| Poly(ethylene-co-acrylic acid) | Clear | Very Hard | H = 2.5 mm, r = 1.5 mm | Ovoid |
| Poly(vinyl-alcohol-co-ethylene) | Clear | Very Hard | H = 3 mm, r = 1 mm | Cylindrical |
| Poly(vinyl-alcohol-co-ethylene) | Clear | Very Hard | H = 3 mm, r = 1 mm | Cylindrical |
| Liquid Crystal Polymer 30% | Opaque Cream | Very Hard | H = 4 mm, r = 1 mm | Cylindrical |
| Trans ABS | Clear | Very Hard | H = 3 mm, r = 1 mm | Cylindrical |
| Cyclic Olefin Copolymer | Clear | Very Hard | H = 3 mm, r = 1 mm | Cylindrical |
| Acetal Hostraform | White Opaque | Very Hard | H = 2 mm, r = 2 mm | Convex Disc |
| Polyester | White Opaque | Very Hard | H = 3 mm, r = 1 mm | Cylindrical |
| Polyetherimide | Yellow transparent | Very Hard | H = 3 mm, r = 1 mm | Cylindrical |
| Polyethylene | Clear | Very Hard | H = 3 mm, r = 1 mm | Cylindrical |
| Nylon | White Opaque | Very Hard | H = 3 mm, r = 1 mm | Cylindrical |
| Polyether Polyurethane | Clear | Almost elastomeric | H = 3 mm, r = 1.5 mm | Cylindrical |
| Styrene Butadiene block copolymer | Clear | Very Hard | r = 4 mm | Spherical |
| Polypropylene random copolymer | Semi transparent | Very Hard | r = 4 mm | Spherical |
| Ethylene-vinyl acetate | Clear | Medium Hardness | r = 4 mm | Spherical/Convex disc |

Sampling Methods

A variety of methods were used to evaluate the suitability of various plastics for the analysis of unpurified samples:

1) Vortex method; a fresh buccal scrape was taken using an omniswab (Whatman Ltd). UV cleaned plastic samples were placed in a 6 ml sterile bijou tube with swab sample and mixed at high speed for 10 secs with a vortex in order to contact the plastic sample with the nucleic acid containing material. The plastic was then transferred to a reaction vessel using sterile fine-point tweezers.

2) Rubbing method; UV cleaned plastic samples were held between a clean set of fine-point tweezers. These were then used to rub one of the surfaces of the plastic against a sample (eg, dried blood stain on fabric/glass, dried saliva stain on fabric/glass etc) in order to contact the plastic with the nucleic acid containing material. The plastic sampling surface was then transferred to a reaction vessel with the rubbed surface faced downwards into the reaction mix. The plastic surface was left in situ in both methods.

described in the kit's user manual but using a half volume reaction. The half volume reaction mix uses the following reaction set-up per sample; 10.5 μl AmpFlSTR PCR Reaction Mix, 5.5 μl AmpFlSTR SGM plus Primer Set, 0.5 μl. 15 μl of reaction mix and 10 μl of water were added to each sample for a total reaction mix volume of 25 μl.

Amplification and interrogation of target sequences was performed using an Applied Biosystems 9700 instrument (Applied Biosystems). Following an initial denaturation to activate the hotstart enzyme (95° C. 11 minutes), targets were amplified using 28 cycles comprising denaturation (95° C. 1 minute), primer annealing (59° C. 1 minute) and extension of products (72° C. 1 minute). After amplification, product adenylation was carried out (60° C. 45 minutes). Samples were subsequently held at 4° C. until required for further processing.

Amplification and interrogation of target sequences was performed using an Applied Biosystems 3100 (Applied Biosystems). For analysis 1 μl of amplified product was added to 8.9 μl of Hi-Di Formamide (Applied Biosystems) and 0.1 μl of Genescan 500 ROX size standard. Samples were injected into a 36 cm capillary array at 3 kV for 10 seconds. Samples were analysed using Genemapper ID.

STR Analysis Using HyBeacon Probes

Amplification and interrogation of STR targets was performed based on the method published by French et al 2008 (Ref 1), utilising fluorescent oligonucleotide probes, non-fluorescent blocker oligonucleotides and melting curve analysis.

PCR volumes were 20 µl comprising 1× SpeedSTAR Buffer I (TaKaRa) or 1 unit Phire Buffer (Finnzymes), 1 unit SpeedSTAR polymerase (TaKaRa) or 1 unit Phire Polymerase (Finnzymes), 3% BSA (Roche), 0.5% Tween-20 (Sigma) and 1 mM dNTPs (0.25 mM each—GE Healthcare, Amersham, UK). Depending on the assay performed (i.e. D16S539 or D18S51), 1 µM forward primer, 0.1 µM reverse primer and 75 nM of probe for the appropriate test was used. D16S539 and D18S51 assays also contained 1 µM and 375 nM of non-fluorescent blocker, respectively. Asymmetric PCR was utilised to generate an excess of the target strand such that probe hybridisation was favoured over annealing of amplified sequences (see WO 2007/010268 A2).

Amplification and interrogation of target sequences was performed using Rotor-Gene 6000 (Corbett Research) and CFX96 (Bio-Rad) instruments. Following an initial denaturation to activate the hotstart enzyme (95° C. 1 minute), targets were amplified using 50 cycles comprising denaturation (95° C. 1 seconds), primer annealing (64° C. 4 seconds) and extension of products (72° C. 4 seconds). Following amplification, reactions were denaturated (95° C. 1 minute) and cooled (20° C. 2 minutes) prior to melting curve analysis.

Melting curve analysis was performed by heating reactions from 20° C. to 70° C., acquiring fluorescence at 0.5° C. increments with 5 second dwell times at each temperature. Melting peaks were constructed by plotting the negative derivative of fluorescence with respect to temperature (−dF/dT on the y-axis) against temperature x-axis).

SLC6A4 Gene Analysis and List of Oligonucleotides Used

Amplification and detection of polymorphic SLC6A4 gene targets was performed based on a Loop Mediated Isothermal Amplification (LAMP) method as described by Masaomi Iwasaki, Toshihiro Yonekawa, et al (2003)[2]. The intercalating fluorescent dye EvaGreen was used to detect target amplification in real-time and through melting curve analysis.

PCR volumes were 25 µl comprising 1× Isothermal Mastermix (Genesys), 0.8 µM Inner primers, 0.2 µM outer primers, 0.2 µM loop primers.

Amplification and interrogation of target sequences were performed using a CFX96 (Bio-Rad) instrument. Targets were amplified by incubating samples at 59° C. for 30 minutes using a CFX96 instrument (Bio-Rad), acquiring fluorescence every 30 seconds. Following amplification, reactions were denaturated (95° C. 3 minutes) prior to melting curve analysis.

Melting curve analysis was performed by heating reactions from 40° C. to 90° C., acquiring fluorescence in the FAM channel at 0.5° C. increments with 5 second dwell times at each temperature. Melting peaks were constructed by plotting the negative derivative of fluorescence with respect to temperature (−dF/dT on the y-axis) against temperature x-axis).

Generation of Soxhlet Extracted PDMS Surfaces and Reference to Method

PDMS surfaces were cleaned of unbound siloxane with ethanol within a soxhlet extractor. The method used was based around that described by Thibault et al (2007)[3].

To test the effect of unbound siloxane, approximately 20 PDMS surfaces were placed into a porous thimble within a 100 ml soxhlet device. The soxhlet device was placed into a 250 ml beaker with 180 ml of absolute ethanol. The Soxhlet device was set up to reflux approximately 8 times an hour for a 12 hour period. No weighing of the materials and reagents was carried out as the extracted siloxane is of no further interest to the experiment. Unbound siloxane-free surfaces were used as described above.

Generation of the KOH Modified Surfaces

PMMA surfaces were KOH etched by stirring the surface in a 1M KOH (potassium hydroxide) for 24 hours at 85° C. To test whether the modification had occurred the surfaces where shaken (modified and native) in a 0.1% malachite green in water. After incubating for 10 minutes the supernatant was removed and the beads washed excessively with water. Due to the carboxyl groups at the surface of the modified beads, the positively charged dyes are kept, whereas the native beads do not bind any dye. Successfully modified beads appear green.

Example 2

Evaluation of Plastic Materials for Generation of Swab Devices

Various plastic (as indicated in FIG. 1) bead shapes of varying sizes were vortexed briefly with mouth-swabs (Omniswabs, Whatman) and then placed into the commercial PCR reaction kit designed to detect 10 different short tandem repeat types plus an amelogenin sex test (AmpflSTR© SGMplus™; Applied Biosystems). The reaction utilised the manufacturer's recommended cycling conditions, in a half volume 25 µL reaction. The PCR products generated were separated by capillary electrophoresis using an Applied Biosystems 3100 instrument. FIG. 1 demonstrates that certain plastics (Topes, Acrylic, Crystal Polystyrene, Polypropylene, HDPE, Polycarbonate, Medium impact Polystyrene, PVC, Liquid Crystal Polymer 30%, Trans ABS, Cyclic Olefin Copolymer, Acetal copolymer, Polyester, Polyetherimide, Polyethylene, Nylon, Polyether Polyurethane, Styrene Butadiene block copolymer, Polypropylene random copolymer and Ethylene-vinyl acetate) have collected, transferred and suitably enabled cells from the mouth-swabs to be made available for DNA. In standard applications of this technology a peak height of over 25 rfu is considered to reflect real PCR product above the background (Custodian Document; CUSTP-GS-003). It can be seen that contact with a variety of plastics enables significant levels of detection. The observation in this study that some plastics did not work (e.g. Poly-ethylene-block-polyethylene glycol, Poly(ethylene-co-acrylic acid), Poly(Vinyl-alcohol-co-ethylene, Poly (Ethylene-co-vinyl-acetate) graft maleic anhydride) indicates that the observed positive results were not due to an artefact of mechanical shear of cells from the swab onto the plastic. Data was produced from three separate samples obtained from one individual. All products amplified from plastic materials were specific to the swab donors. DNA fragments up to and over 350 base pairs were successfully detected (determined by the donor's STR type), suggesting that plastic materials do not inhibit PCR when left in the reaction tube.

FIG. 1 demonstrates that a range of plastic materials are suitable for adsorption of biological materials and that efficiency varies depending on material type.

Example 3

Evaluation of Plastic Materials for Generation of Swab Devices

Figure 2:
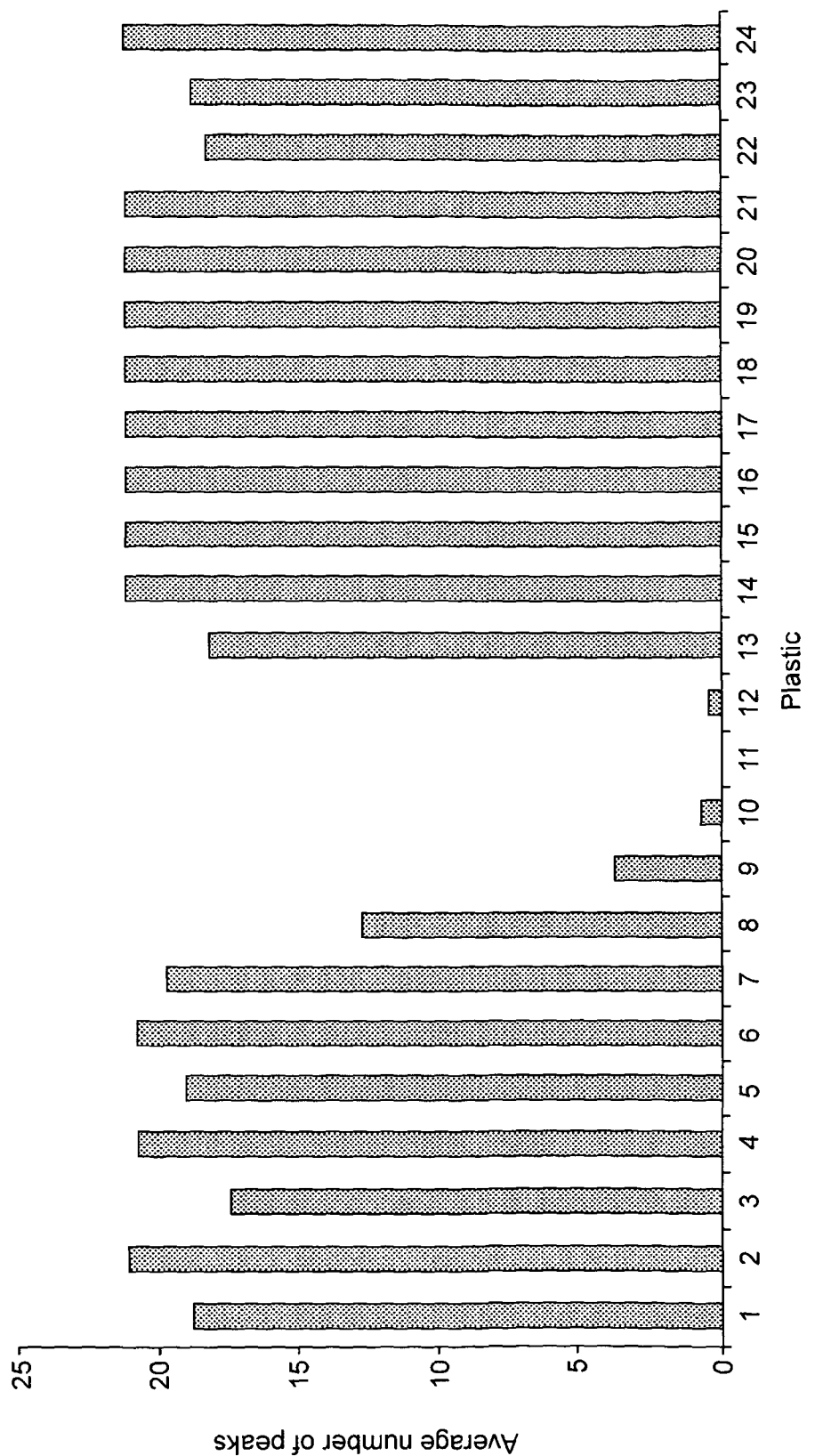

Experimental conditions as for Example 2. This study examines whether the 10 different short tandem repeat PCR reactions plus the amelogenin locus were all detected in the multiplex reaction. If all targets are successfully amplified then 21 DNA products should be detected. FIG. 2 demonstrates that a range of plastic materials are suitable for adsorption of biological materials and that efficiency varies depending on material type. The most efficient were Tapas, Acrylic, Crystal Polystyrene, Polypropylene, HDPE, Polycarbonate, Medium impact Polystyrene, PVC, Liquid Crystal Polymer 30%, Trans ABS, Cyclic Olefin Copolymer, Acetal copolymer, Polyester, Polyetherimide, Polyethylene, Nylon, Polyether Polyurethane, Styrene Butadiene block copolymer, Polypropylene random copolymer and Ethylene-vinyl acetate. The worst performers were Polyethylene-block-polyethylene glycol, Poly(ethylene-co-acrylic acid), Poly (Vinyl-alcohol-co-ethylene, Poly(Ethylene-co-vinyl-acetate) graft maleic anhydride.

Example 4

Evaluation of Plastic, Silicone, Thermoplastic Elastomers (TPE) and Glass as Materials for Use Within a HyBeacon Assay PMMA (Acrylic plastic), PDMS (Silicone) and Santoprene (a TPE) surfaces of uniform size were rubbed on blood and saliva-stained glass and fabric with clean sterile tweezers. As described in the second part of the sampling details, samples were subsequently placed within PCR reactions containing a singleplex PCR amplification for the Short tandem repeat loci called D16S539 (D16S539). The assay (akin to that described in French et al (2008)[1]) is a homogeneous reaction containing not only the PCR primers for these loci, but also a distinct fluorescent oligonucleotide probe (D16S539 probe labelled with fluorescein dT) and competing 'blocker' oligonucleotide, which is described in detail above. Following PCR amplification, the reaction is then processed through a temperature range, commonly known as a 'melting curve' (see x-axis scale of figure) and the rate of change of fluorescence is plotted to demonstrate the dissociation of the bound probe from its target. The results indicate that plastic, silicone and TPE surfaces provided sufficient cell contact to allow samples to be placed directly into the reaction not only to support the correct PCR amplification but also without interfering with the subsequent hybridisation and fluorescence analysis. Only a D16S539 STR repeat 'type' 11 was expected for the analysis in the D16S539 FAM fluorescence channel as observed.

Figure 3:
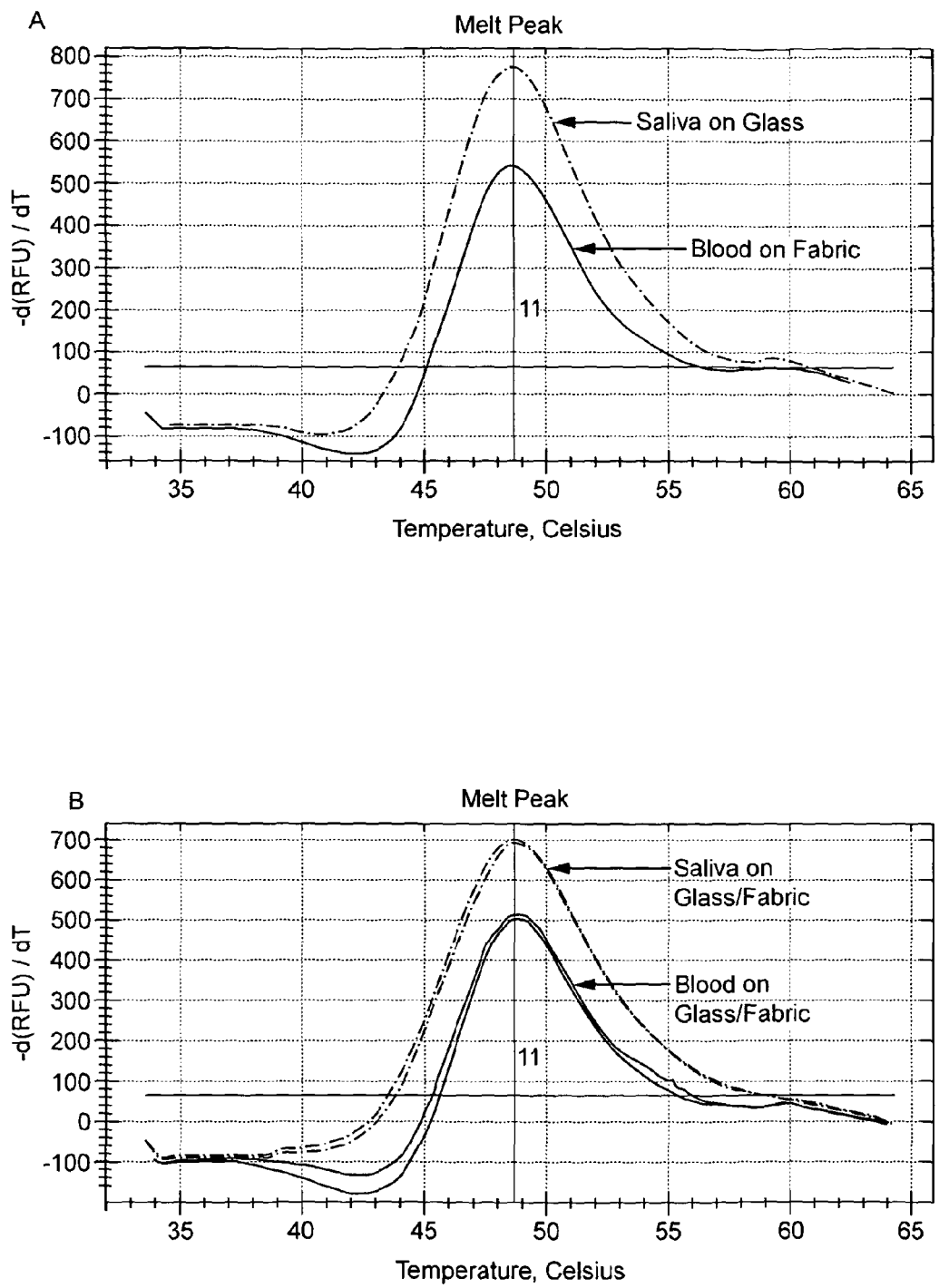
Figure 3:
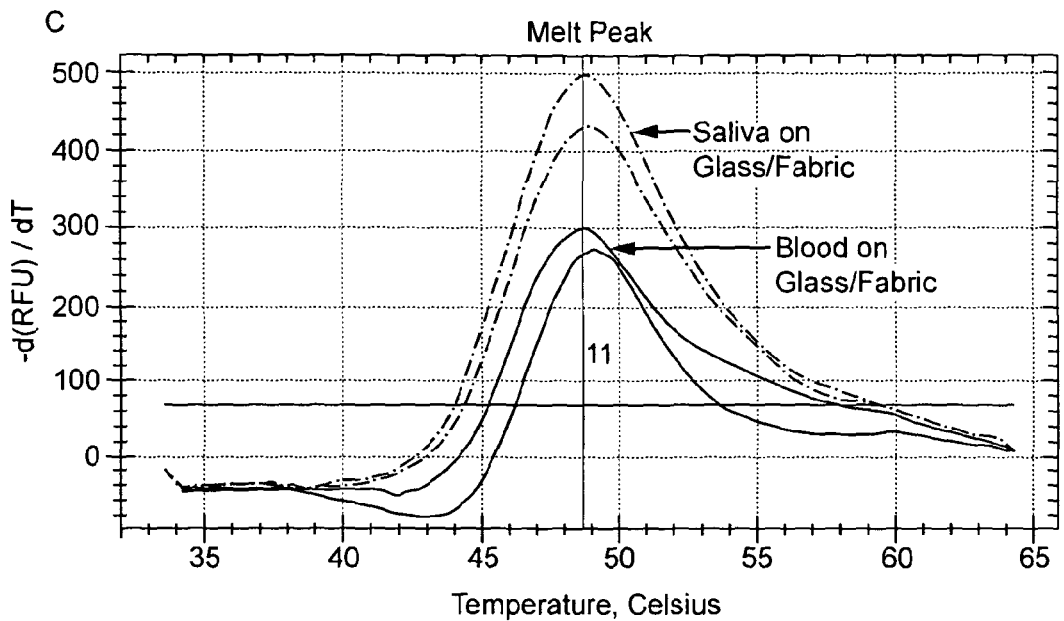

This experiment used different PCR primers and temperature cycling conditions to those described in FIGS. 1 & 2, and included probe and blocker oligonucleotides not present in these experiments, thus demonstrating that binding of DNA to the plastics, silicones and TPE contact surfaces are not PCR reaction specific, inhibitory to the fluorescent detection nor to the complex hybridisation procedures taking place (by reference to control DNA only input samples as indicated), as shown in FIG. 3.

Figure 25:
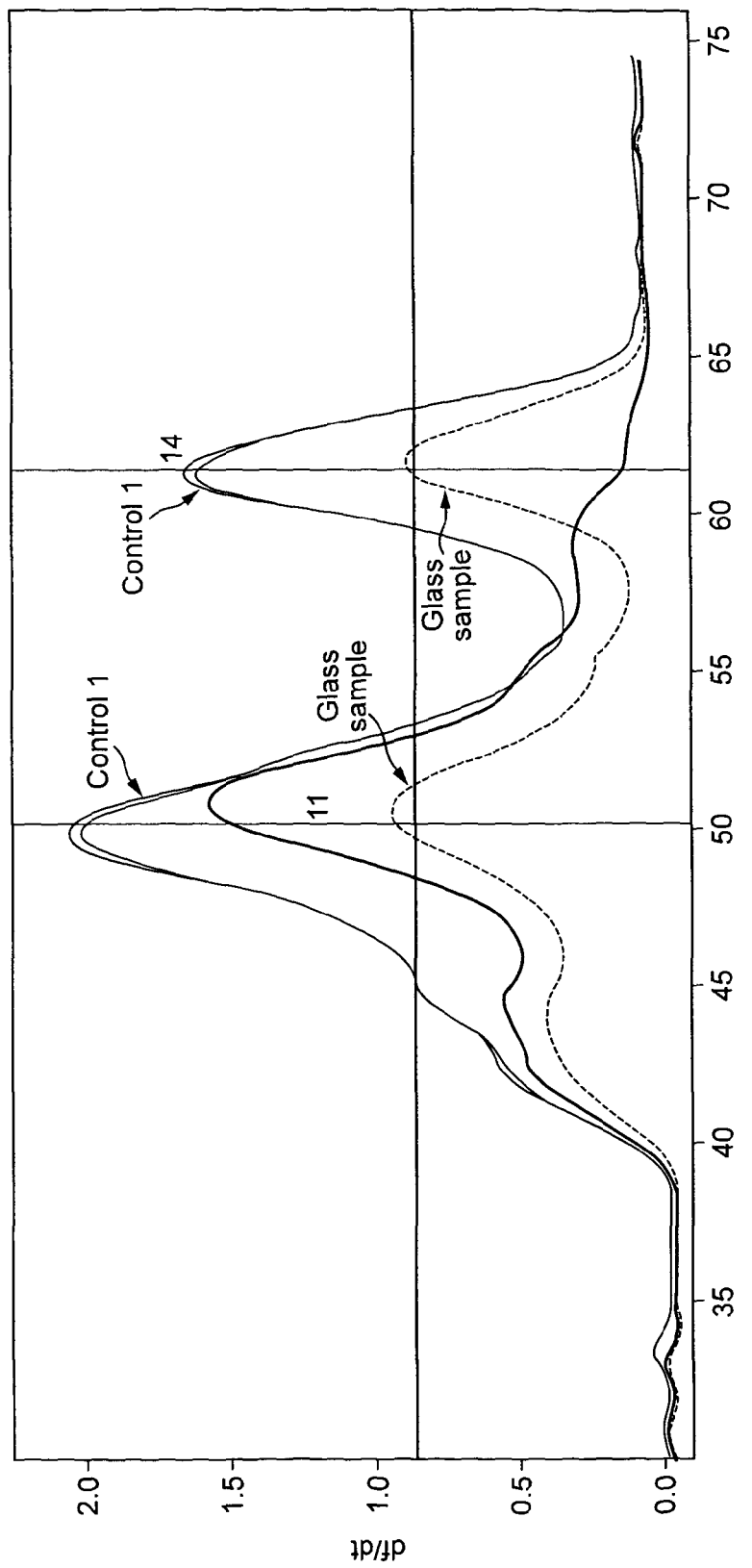
FIG. 25 shows that glass can be used to obtain nucleic acid-containing material from a sample and not interfere with an amplification reaction.

Unmodified 1.5 mm glass beads were rubbed on dried buccal swabs. DNA control and swab results are shown in FIG. 25. The peaks indicated as 11 and 14 are the STR types of the D16S539 typing assay.

Example 5

Figure 4:
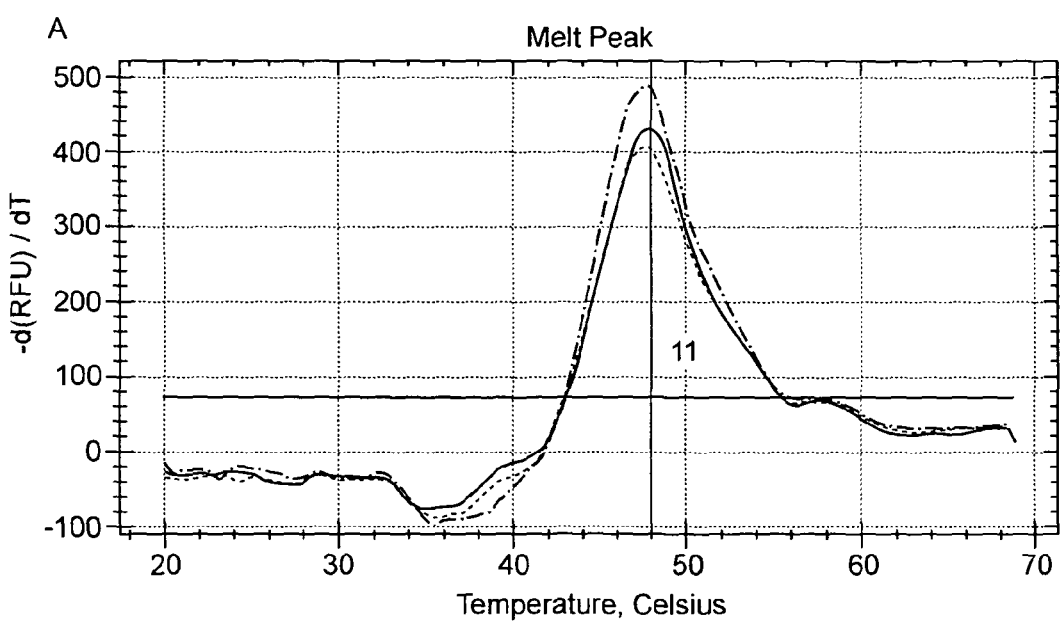
Figure 4:
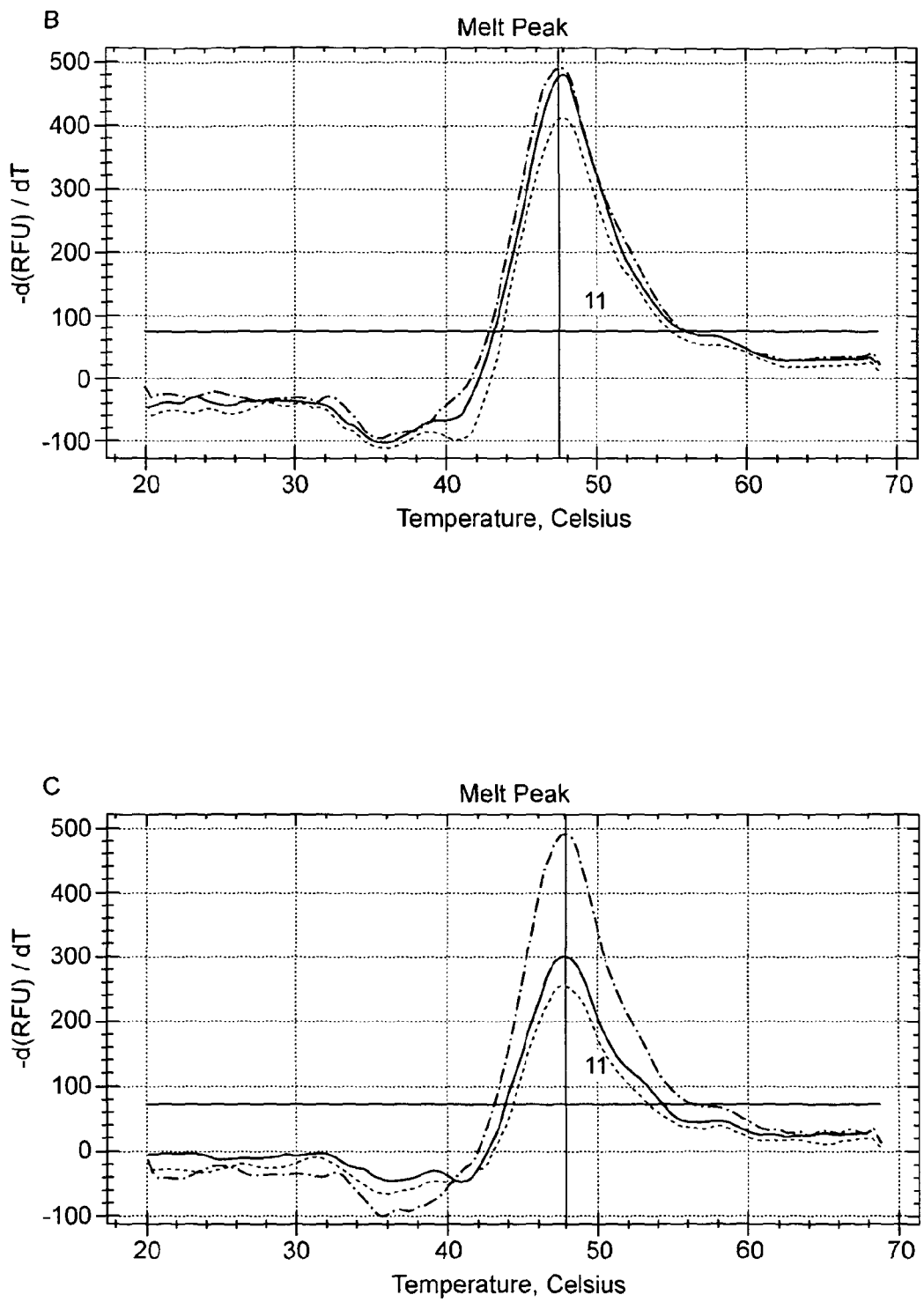

Evaluation of Plastic, Silicone and Thermoplastic Elastomers: Effect on the Efficiency of Amplification Clean PMMA, PDMS and Santoprene surfaces were placed into reaction vessels containing a D16S539 HyBeacon assay as described in the above material and methods section. 2 ng of extracted DNA was added to each reaction containing the sampling surfaces. These were compared to a control D16S539 HyBeacon assay with a template of 2 ng of extracted genomic DNA without a sampling surface present. Only a STR repeat 'type' 11 was expected for the analysis in the D16S539 FAM fluorescence channel as observed. No difference was observed between the control reaction and the PDMS and PMMA-mediated reaction. There was a reduction in peak height observed in the reaction using Santoprene as a transfer medium. This may be due to the opaqueness of the material blocking fluorescence detection. PMMA and PDMS do not affect the efficiency of the D16S539 HyBeacon assay, as shown in FIG. 4. Santoprene reduces the strength of the signal obtained.

Example 6

Figure 5:
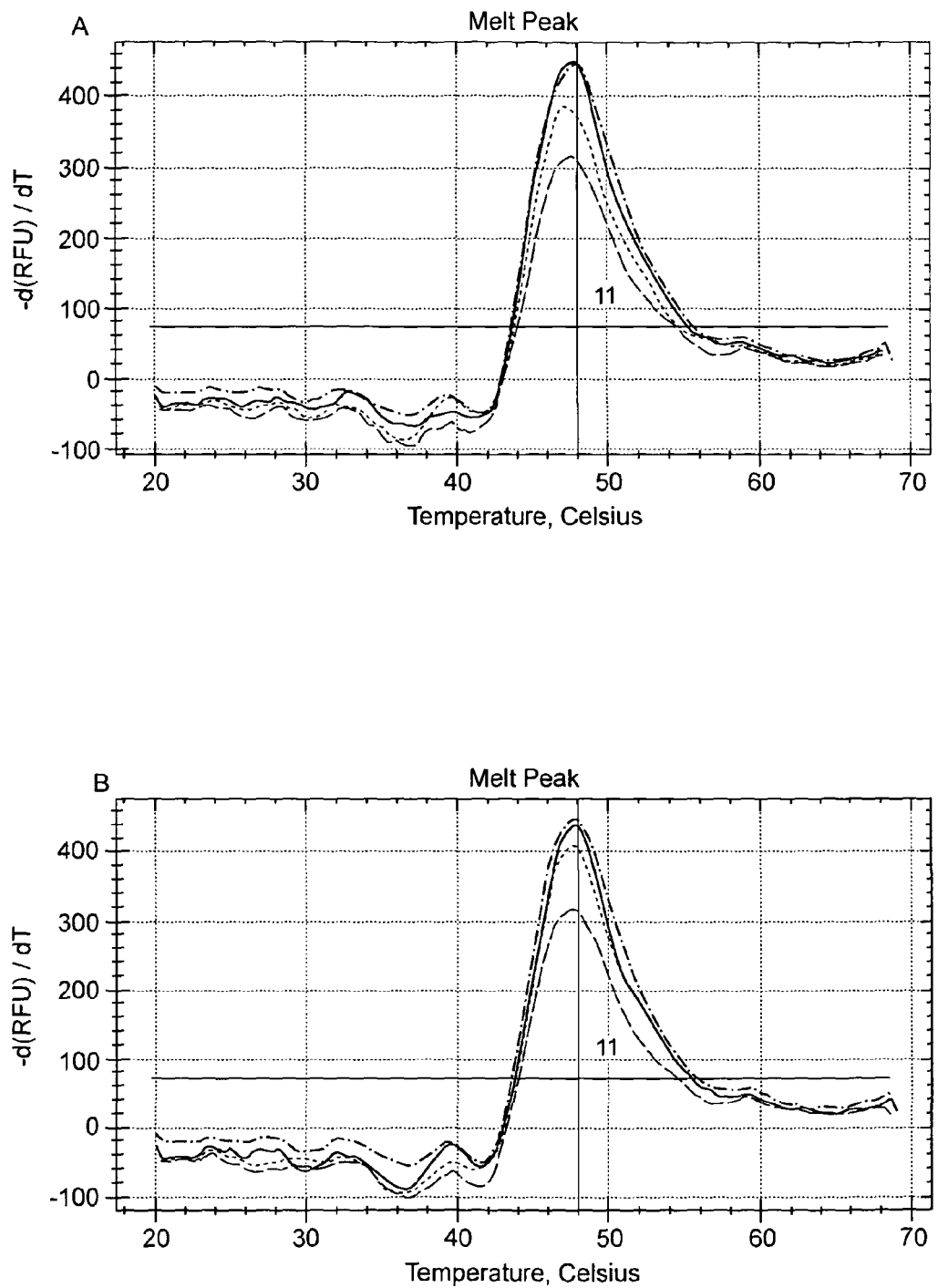
Figure 5:
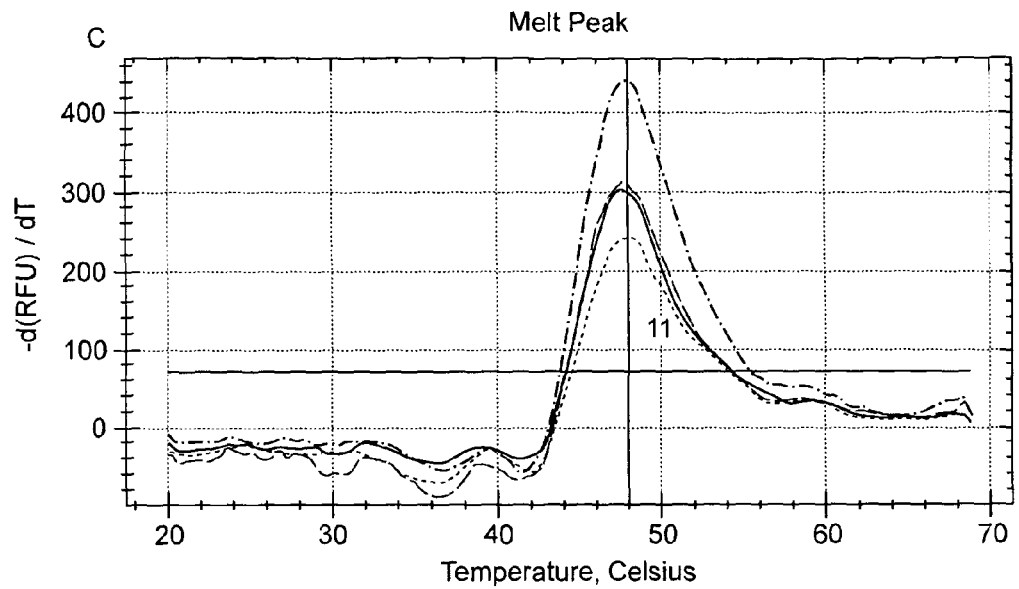

Evaluation of Plastic, Silicone and Thermoplastic Elastomers: Effect on the Efficiency Cell Lysis in Un-Extracted Biological Samples Clean PMMA, PDMS and Santoprene surfaces were placed into reaction vessels containing a D16S539 HyBeacon assay as described in the above material and methods section. Buccal swabs (Omniswab, Whatman) were expressed by vortexing in 500 µl of water diluent. 2 µl of expressed swabs were compared with 2 ng of extracted DNA without a sampling surface present. Only a 'type' 11 was expected for the analysis in the D16S539 FAM fluorescence channel as observed. Very little difference was observed between the control reaction and the PDMS and PMMA reaction. There was a reduction in quality of products generated using Santoprene transfer. This may be due to the opaqueness of the material. PMMA and PDMS do not alter the amplification of un-extracted cellular material in a D16S539 HyBeacon assay, as shown in FIG. 5. Santoprene reduces the strength of the signal obtained. This further backs up the idea associated with opaque surfaces.

Example 7

Figure 6:
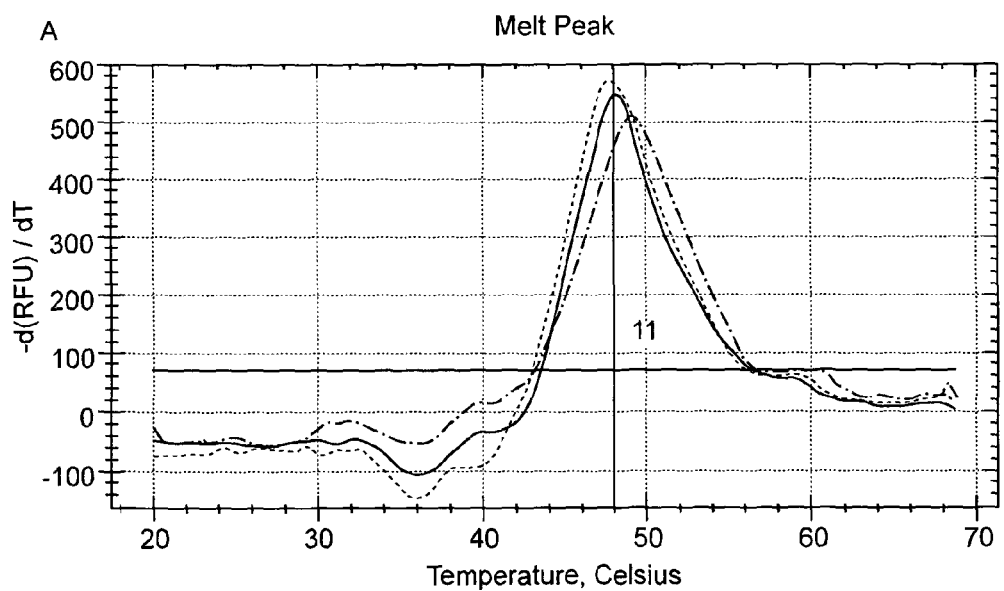
Figure 6:
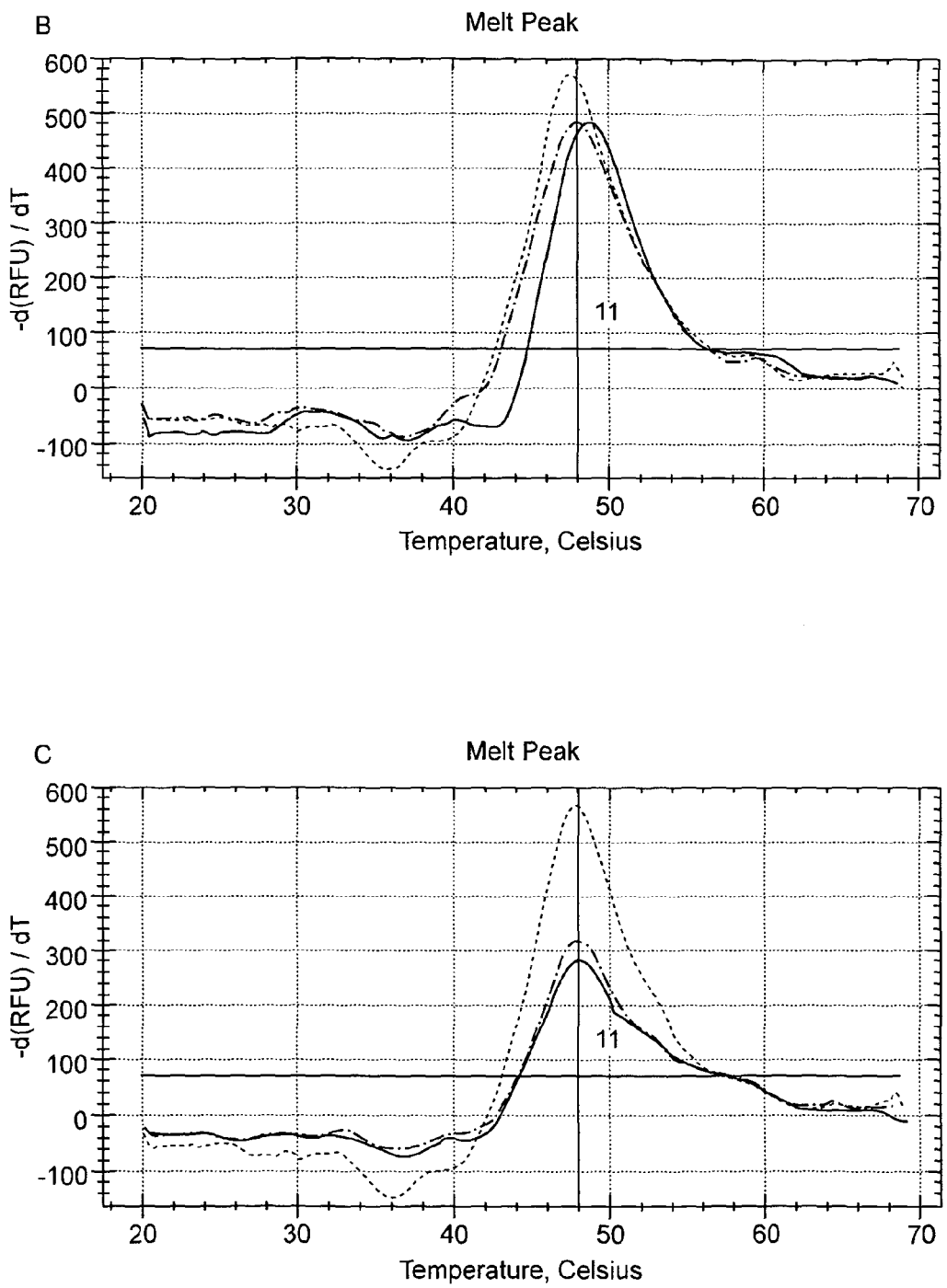

Evaluation of the Binding of Biological Material to Plastic, Silicone and a Thermoplastic Elastomer for Use in Multiple Reactions Clean PMMA, PDMS and Santoprene surfaces were rubbed onto a dried saliva stain on a clean and previously untouched glass slide. Samples were analysed using the D16S539 HyBeacon assay as described in the above material and methods section. The results for these are shown in FIG. 6. After amplification the reagent mix was removed from the reaction vessel and discarded, the sample surface was then gently washed by pipette aspiration with tissue culture water to remove any residual D16S539 assay components and amplified products. The surfaces were allowed to dry and then transferred to clean reaction vessels. Cleaned sample surfaces were then used as templates for the D18S51 HyBeacon assay, as described in the above material and methods section, to determine whether sufficient biological material remained on the surface to facilitate analysis of a second independent target sequence. The D18S51 target is on a separate chromosome from the D16S539 target, the D18S51 probe will not detect amplified D16S539 targets and D16S539 reagents will not amplify D18S51 targets. The D18S51 test also uses a different dye label to the D16S539 probe ensuring that the two tests are completely independent of each other.

Figure 7:
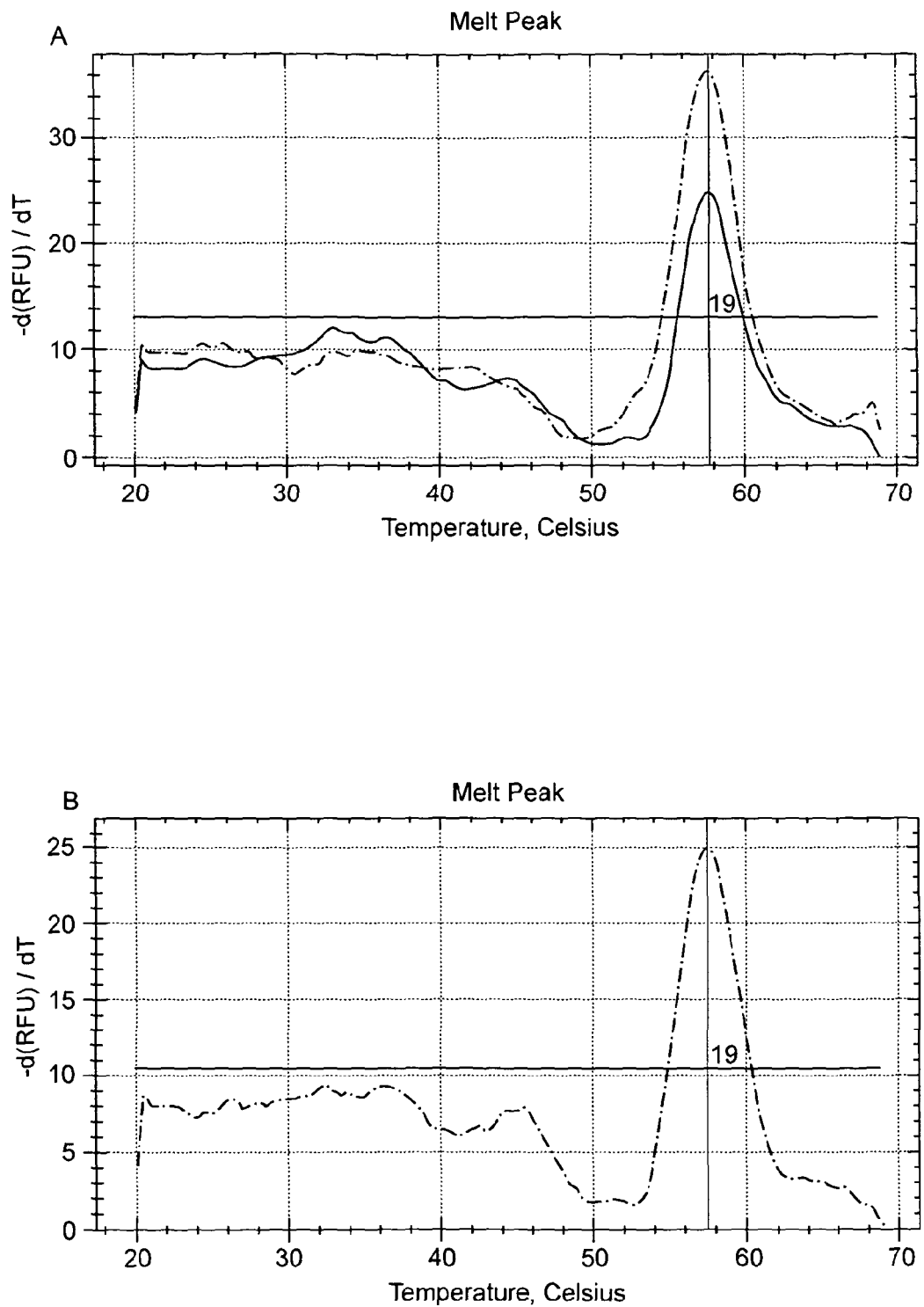
Figure 7:
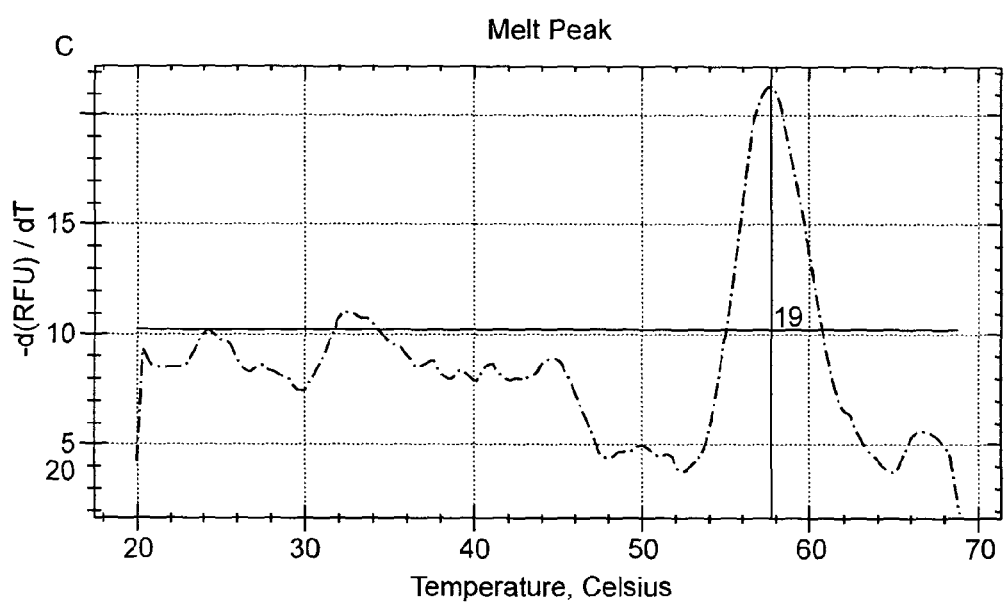

FIG. 7 shows that the transferred surfaces had enough biological material adsorbed on the sampling surface to permit amplification of the second target sequence. Only a 'type' 11 was expected for the analysis in the D16S539 FAM fluorescence channel as observed, and only a 'type' 19 was expected for the analysis in the D18S51 TAMRA fluorescence channel as observed. The D16S539 and D18S51 tests yielded melting peak Tms Of Considerably Different Tms.

EXAMPLE 8

Figure 8:
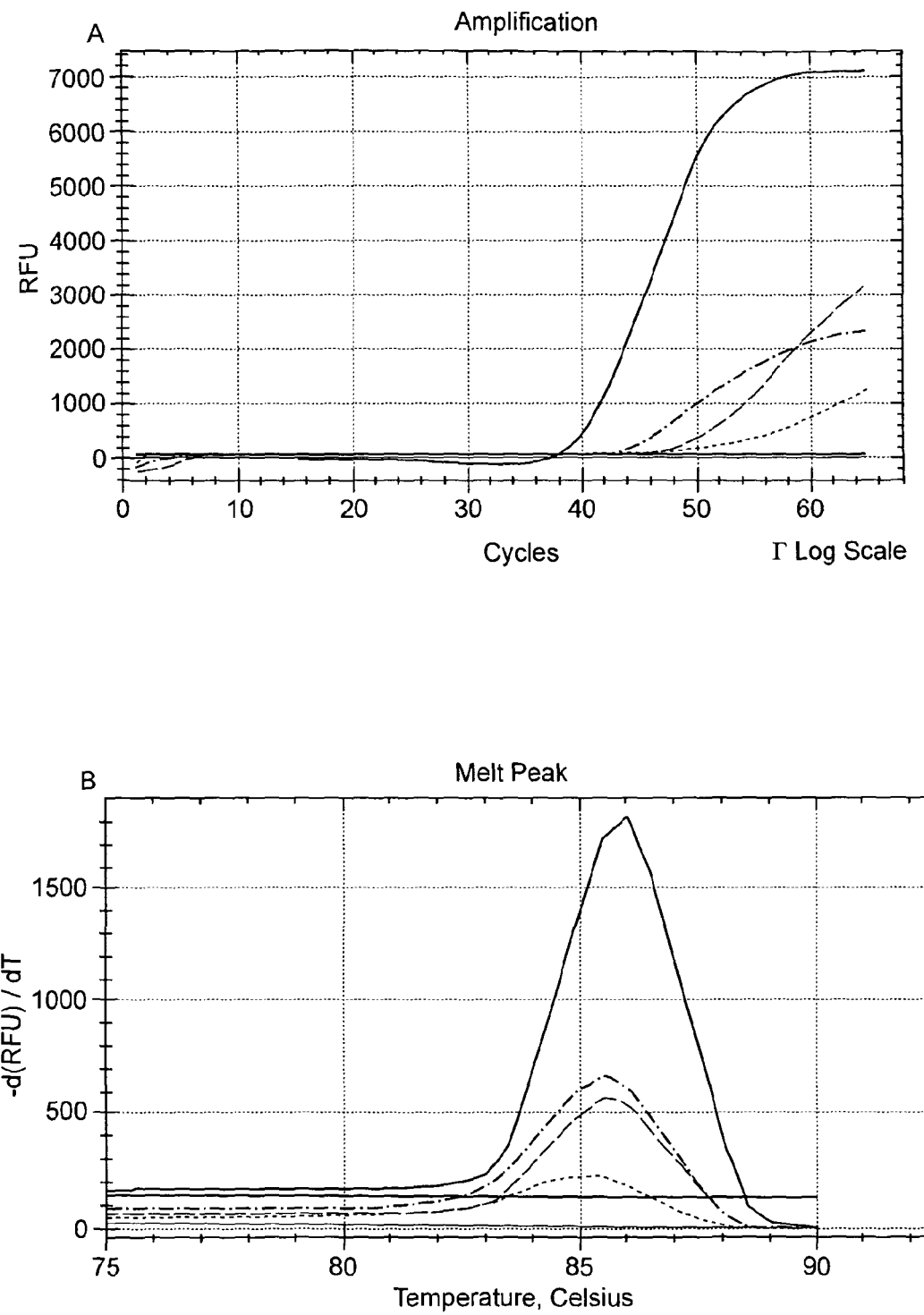
FIG. 8 shows A) Amplification curves and B) melting peaks obtained using a Loop-Mediated Isothermal Amplification (LAMP) test to analyse a section of the SLC6A4 gene. Samples were obtained by rubbing PDMS on a dried saliva stain on glass.

Evaluation of the Effect of the Initial 95° Denaturation Step of Amplification on the Promotion of Cellular Material Being Available for Amplification A clean PDMS surface was rubbed on a glass slide stained with a saliva sample, as described in the above material and methods section. PDMS surfaces were analysed in triplicate with a Loop-mediated Isothermal amplification (LAMP, Eiken) test designed to amplify and detect SLC6A4 target sequence. This assay incubates the amplification reagents at 59° C. for 30 mins of isothermal amplification. Amplified product is detected via an intercalating dye. The three PDMS samples were compared to a control, extracted DNA sample from the same donor. The fluorescence melting peaks, shown in FIG. 8, indicate successful target amplification from plastic surfaces.

This suggests the 95° C. denaturation step is not essential for amplification of cellular material bound to PDMS surfaces.

Example 9

Figure 9:
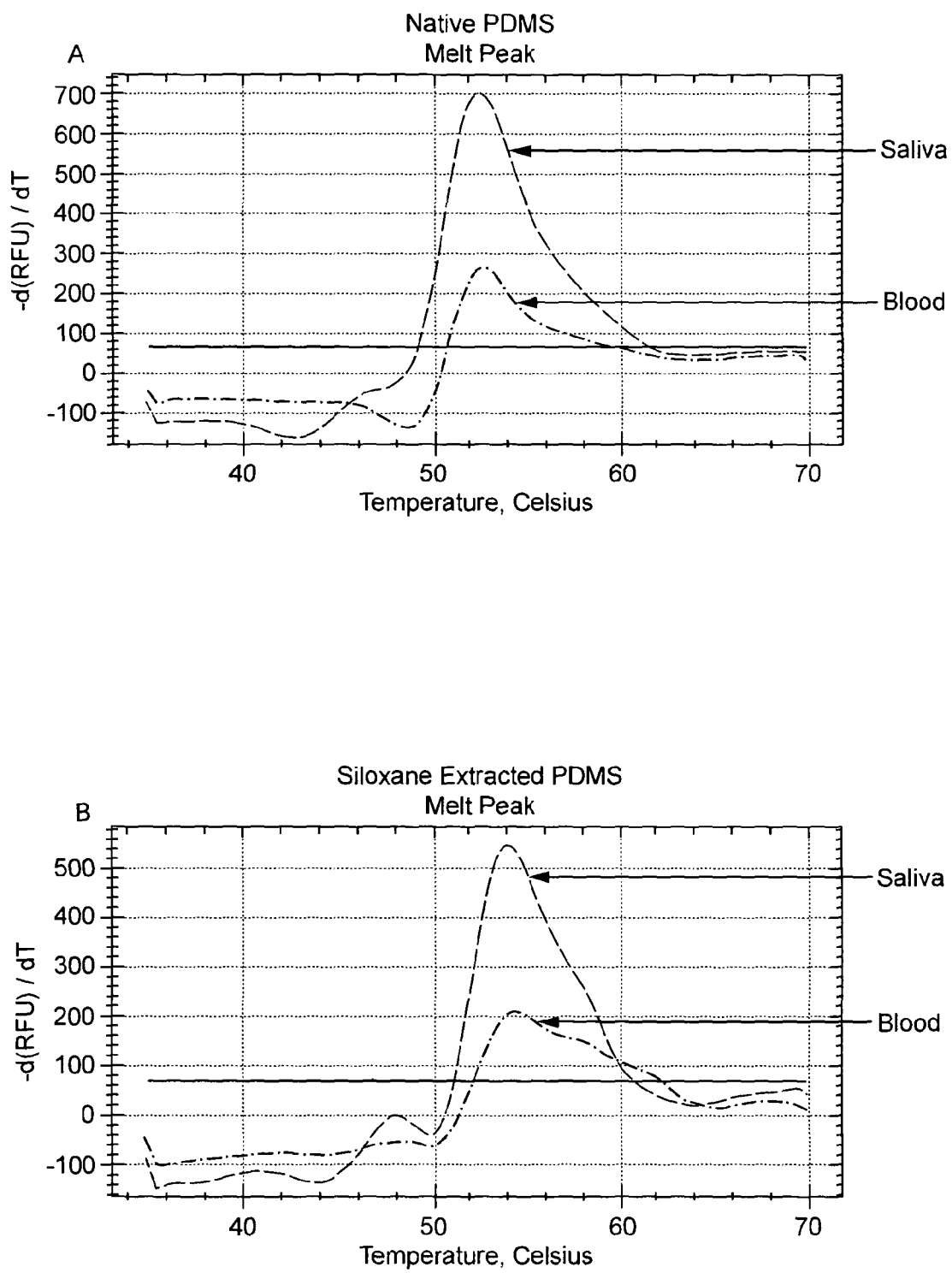
FIG. 9 shows the comparison of PDMS that has had unbound siloxane removed via a Soxhlet extraction with ethanol.

Evaluation of the Effect of Unbound Siloxane Within PDMS on the Binding of Cellular Material The paper by Thibault et al (2007)[3] mentions short chain siloxanes and un-polymerised siloxane as a possible mechanism by which DNA binds to PDMS. Clean PDMS surfaces were placed into a soxhlet device and refluxed with ethanol for a twelve hour period at a rate of approximately 8 flushes an hour. The soxhlet extracted PDMS surfaces were held in DNA-free sterile tweezers and rubbed across a dried saliva stain on a previously untouched clean glass slide. This was carried out in addition to samples that were rubbed on a dried blood stain on a previously untouched clean glass slide. These were compared to native PDMS surfaces. All samples were transferred to a PCR micro-tube and amplified with a D16S539 HyBeacon assay. All methods are described as above in the material and methods section. The donor sample is expected to produce an 11 allele as observed as shown in FIG. 9. There was no noticeable difference in the results obtained between the native and non-native PDMS surfaces. This shows that unbound siloxanes are not the only mechanism by which biological material is adsorbing to the PDMS surface.

Example 10

Summary of Additional Successful Experiments not Covered in the Exemplification Above Table 2 details other experiments carried out that are not covered by the figures shown above.

| Material | Assay used to test | Matrix tested | Sampling method | Result |
| --- | --- | --- | --- | --- |
| Acrylic | D16S539/D18S51 Duplex Hybeacon | Buccal swab | Vortex | Successful amplification and detection |
| Polypropylene | D16S539/D18S51 Duplex Hybeacon | Buccal swab | Vortex | Successful amplification and detection |
| Acrylic | D16S539 Hybeacon | Dried blood on fabric/glass | Rubbing | Successful amplification and detection |
| Polypropylene | D16S539 Hybeacon | Dried blood on fabric/glass | Rubbing | Successful amplification and detection |
| Closed cell foam hydrophobic | D16S539 Hybeacon | Dried blood/saliva on fabric/glass | Rubbing | Some successful amplification and detection from saliva samples |
| Nylon brush | D16S539 Hybeacon | Dried blood/saliva on fabric/glass | Rubbing | Successful amplification and detection |
| Closed cell foam hydrophobic | SGMplus | Dried blood/saliva on fabric/glass | Rubbing | Poor amplification |
| Nylon brush | SGMplus | Dried blood/saliva on fabric/glass | Rubbing | Poor amplification with blood successful amplification with saliva. |
| PDMS | SGMplus | Dried blood/saliva on fabric/glass | Rubbing | Successful amplification |
| Santoprene (TPE) | SGMplus | Dried blood/saliva on fabric/glass | Rubbing | Successful amplification |
| PDMS | D16S539 Hybeacon | Dried semen on fabric | Rubbing | Successful amplification |
| Santoprene (TPE) | D16S539 Hybeacon | Dried semen on fabric | Rubbing | Successful amplification |

-continued

| Material | Assay used to test | Matrix tested | Sampling method | Result |
| --- | --- | --- | --- | --- |
| PDMS | D16S539 Hybeacon | Fingerprint on Glass | Rubbing | Successful amplification/low level and dependant on donor |
| Santoprene (TPE) | D16S539 Hybeacon | Fingerprint on Glass | Rubbing | Some successful amplification |
| Fragment of pencil eraser (Rubber) | D16S539 Hybeacon | Blood/Saliva on Glass | Rubbing | Failed to amplify |
| Latex | D16S539 Hybeacon | Blood/Saliva on Glass | Rubbing | Failed to amplify |

Example 11

No Effect of UV Irradiation for DNA Sterilization on Sampling and Subsequent Amplification PMMA (Acrylic plastic) 1.64 mm beads with varying UV treatments were rubbed on saliva stains on glass with a clean sterile holder, as described in the second part of the sampling method of Example 1. Samples were subsequently placed within PCR reactions containing a singleplex PCR amplification for the STR locus called D16 (D16S539). The assay (akin to that described in French et al (2008) (Reference 1)) is a homogeneous reaction containing not only the PCR primers for these loci, but also a distinct fluorescent oligonucloetide probes (D16 probe labelled with FAM) and competing 'blocker' oligonucleotides. Following the PCR, the reaction is then processed through a temperature range (see x-axis scale of FIG. 26) and the rate of change of fluorescence is plotted to indicate the presence of successful probing. The results indicate that UV treatment of PMMA has very little impact on the material's ability to collect biological material.

Figure 26:
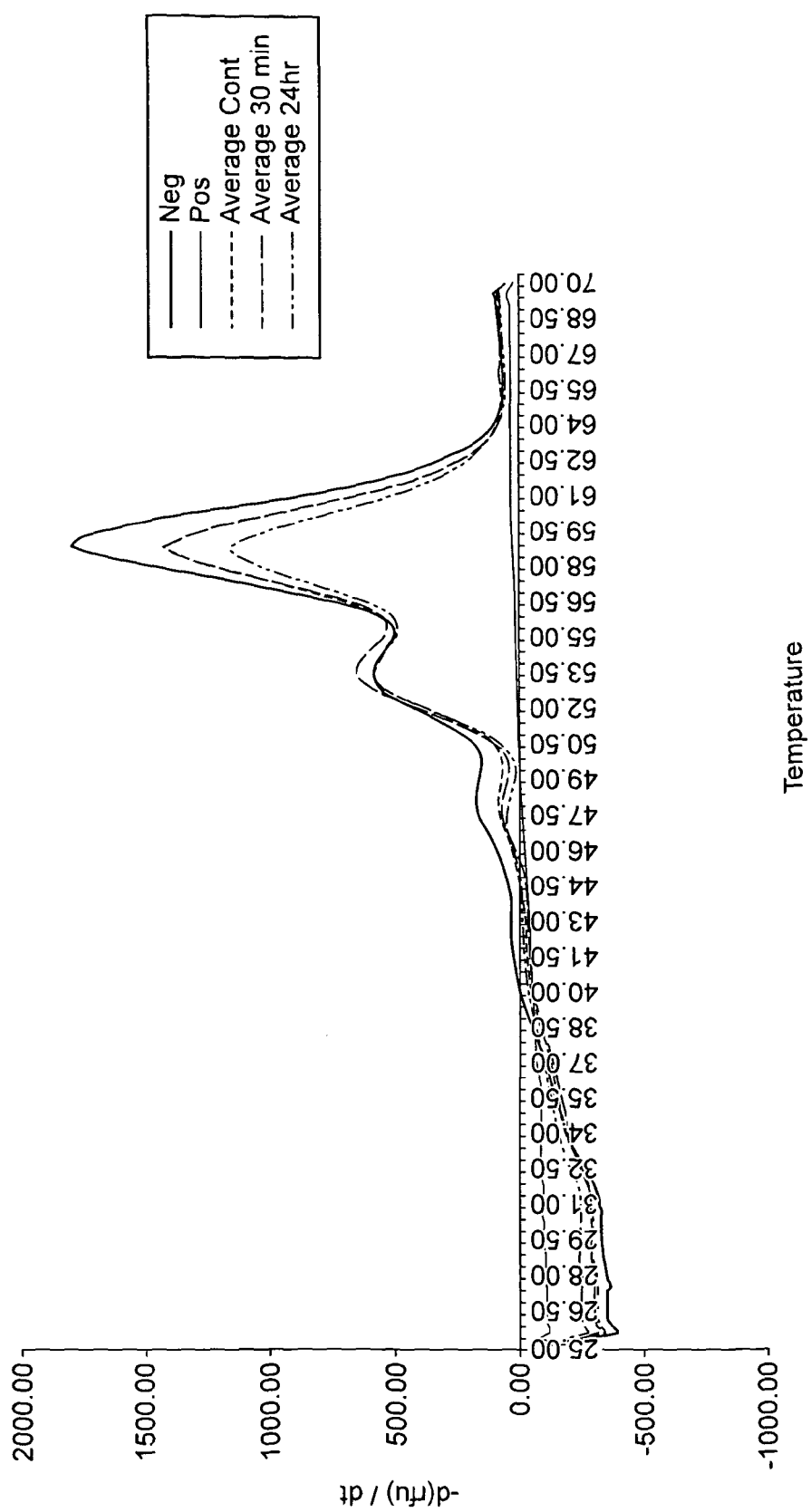
FIG. 26 shows that UV irradiation in order to "DNA sterilize" a polymer does not have any effect on the ability to obtain nucleic acid containing material following contact with a sample and for amplification to proceed.

FIG. 26 shows average melt peaks from 4 replicates of non-UV irradiated PMMA (Average Cont), PMMA UV irradiated for 30 minutes (Average 30 min) and PMMA UV irradiated for more than 24 hrs (Average 24 hr), and obtained from 2.5 ng of DNA (Pos).

Example 12

Effect of KOH Modification to PMMA Surfaces

Figure 27:
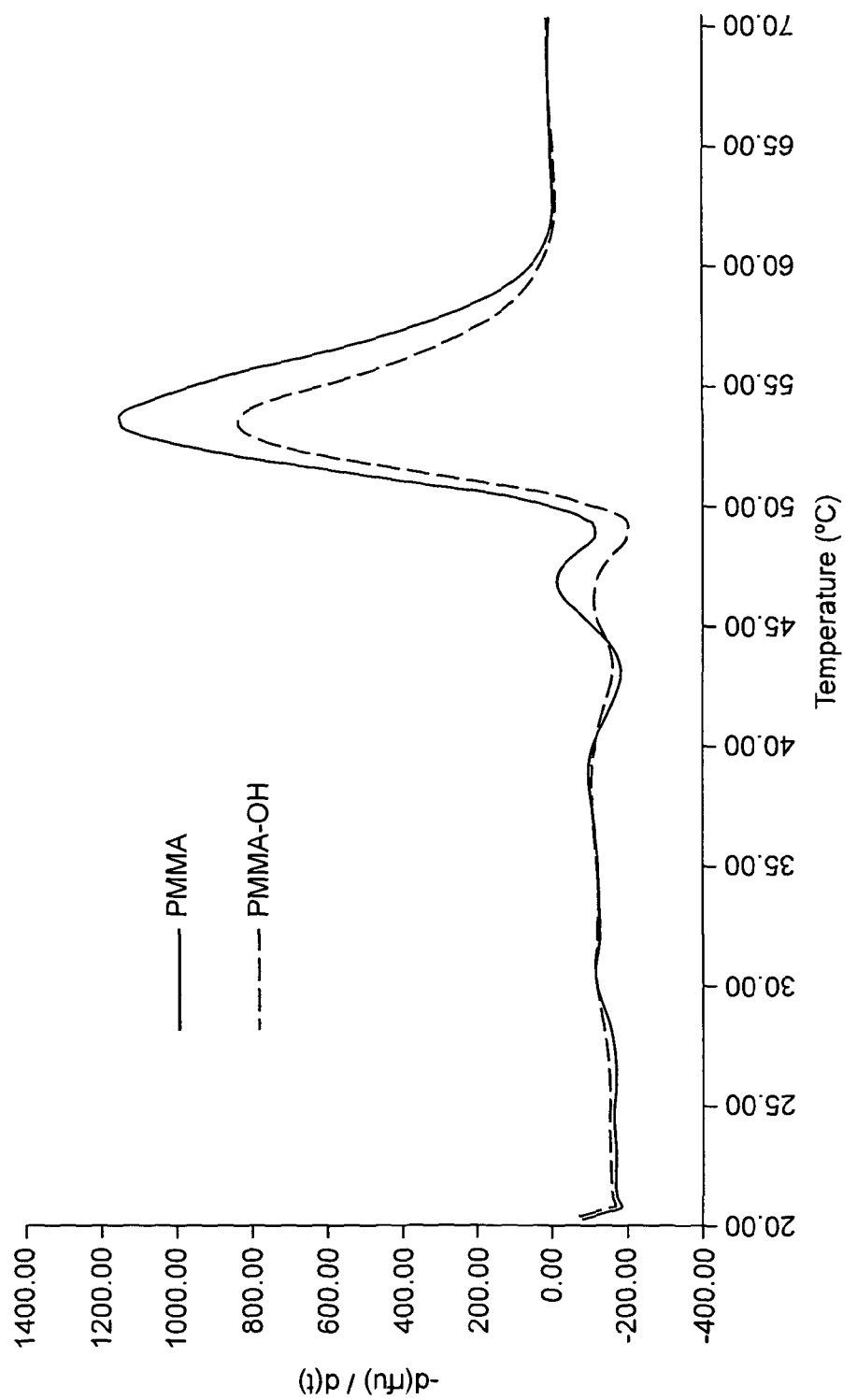
FIG. 27 is a comparison of PMMA with KOH etched PMMA for D16 reaction. Line graphs show average melt peaks taken from eight replicate analyses.

KOH modified and unmodified PMMA surfaces were rubbed on saliva stains on glass with a clean sterile holder. Samples were subsequently placed within Phire based PCR reactions containing the STR locus D16S539. The assay (akin to that described in French et at (2008)) is a homogeneous reaction containing not only the PCR primers for this locus, but also a distinct fluorescent oligonucleotide probe (D16 probe labelled with FAM), and competing 'blocker' oligonucleotides. Following the PCR, the reaction is then processed through a temperature range (see x-axis scale of FIG. 27) and the rate of change of fluorescence is plotted to indicate the presence of successful probing. The results indicate that KOH treatment of PMMA produces a slight reduction in the peak heights obtained.

Apparatus of the Invention

Figure 10A:
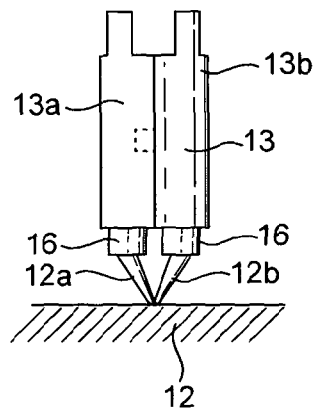
FIGS. 10a-10d are side elevational (FIGS. 10a and 10d), plan (FIG. 10b) and perspective (FIG. 10c) views of parts of a first embodiment of nucleic acid sampling apparatus according to the invention.
Figure 10B:
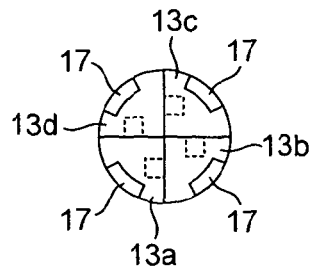
Figure 10C:
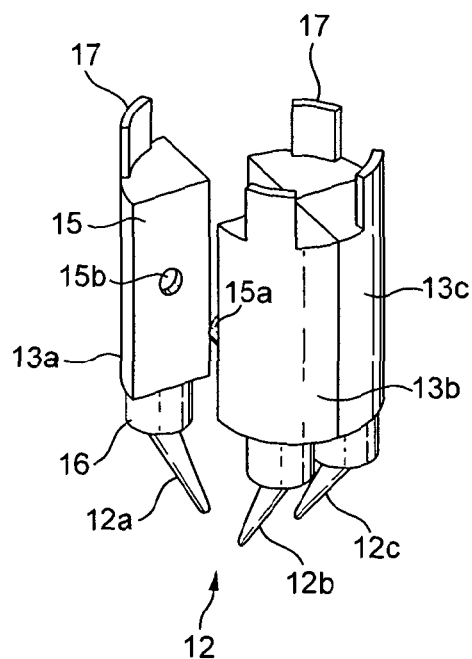
Figure 10D:
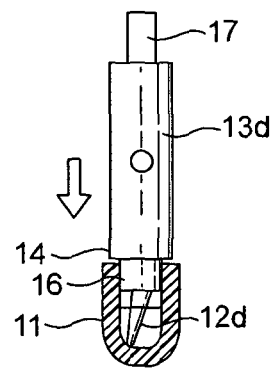
Figure 13:
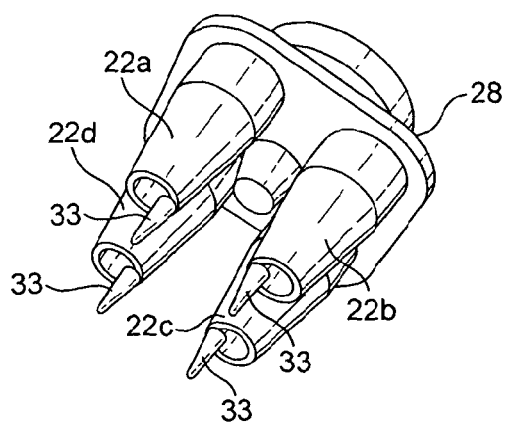
Figure 14:
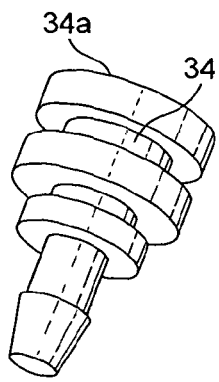
Figure 15:
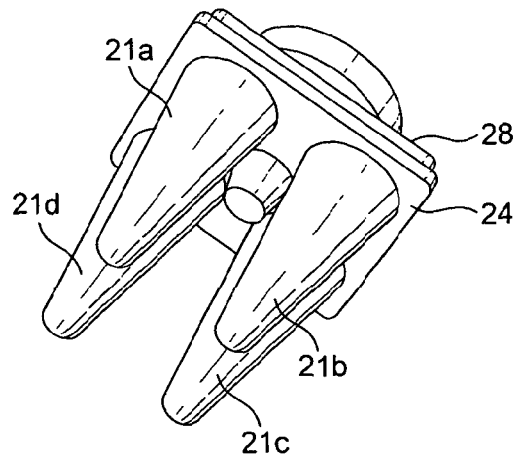
Figure 16:
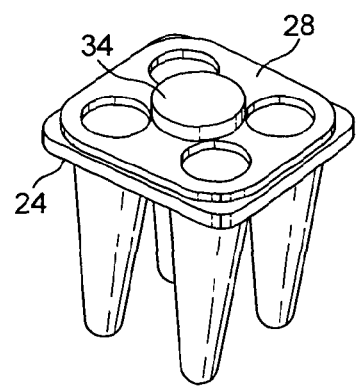

Referring to FIGS. 10a-10d a first embodiment of nucleic acid sampling apparatus 11, 12, 13 in accordance with the invention includes as main components a series of receptacles 11 of which one is visible in FIG. 10d, a plurality of probe elements 12 corresponding in number to the number of receptacles 11 and a manipulator in the form of a transfigurable handle 13. The sampling apparatus 11, 12, 13 of FIGS. 10a-10d, and the further sampling apparatuses described below, are suitable and intended for putting into effect the methods and uses described and defined herein.

The apparatus of FIGS. 10a-10d includes a series of (in the preferred embodiment shown) four hollow, upright, elongate receptacles 11 that each are open at their upper ends to define a respective opening 14.

The openings 14 in the receptacles are sealable in accordance with arrangements described below. The plurality of receptacles 11 preferably are identical to one another and preferably are supported in a line as illustrated in a frame (not shown). The frame supporting the receptacles 11 preferably is of a size that can readily be carried by hand, stored in a briefcase and generally operated manually.

In another arrangement within the scope of the invention the receptacles 11 may be arranged in a square or other polygonal pattern, in a non-straight line or in a circular or oval pattern.

The receptacles 11 may be manufactured from, or at least lined on their interior surfaces with, a polymer that is known to be inert to nucleic acid and reagents used for the amplification reactions mentioned above such that the receptacles 11 do not influence any nucleic acid therein or any amplification reaction. The frame is manufactured from a lightweight material such as a polymer, light metal alloy or a naturally occurring material that does not react with the material of the receptacles 11.

The frame may be made in the alternative from the same material as the receptacles and may be formed simultaneously therewith.

In preferred embodiments of the invention therefore the receptacles 11 may be secured to or formed integrally with the frame such that the frame and receptacles are used and discarded together. Such an arrangement may offer advantages, under some circumstances, in terms of labelling of sample sets, traceability of samples and the generation of proof of disposal or destruction of samples on completion of investigative activities.

In yet further embodiments of the invention, and as illustrated in FIG. 10d, the frame may be dispensed with and the receptacles 11 used in a "stand-alone" manner.

The apparatus of FIGS. 10a-10d as stated includes a plurality of elongate probe elements 12a-12d secured to and supported by an elongate handle 13.

FIG. 10a shows the configuration of the probe elements 12 and handle 13 at the commencement of use of the apparatus for nucleic acid sampling.

The handle 13 includes four (in the embodiment shown, although other numbers are possible within the scope of the invention) handle parts in the form of elongate quadrants 13a, 13b, 13c, 13d.

Each of the quadrants 13a-13d is joined to at least one neighbouring quadrant along an interface extending generally parallel to the direction of elongation of the probe/handle combination 12, 13. The joints are defined by abutting faces 15 of the quadrants formed with mating detent pin 15a and recess 15b combinations that permit releasable securing together of the quadrants 13a-13d. As a result when assembled together the quadrants define a cylindrical handle 13 that may be separated into four distinct, circle segment cross-section handle parts 13a-13d.

In another arrangement within the scope of the invention the handle segments could be connected by so-called "living hinges", ie. hinges of the material of the quadrants that are sufficiently thin as to be flexible and, optionally, frangible.

One face of each of the quadrants 13a-13d is convexly curved. In each case this face lies on the exterior of the joined group of quadrants such that when connected together they collectively define the circular-section handle 13.

Protruding from the in use lower end of each quadrant 13a-13d is a respective probe element 12a, 12b, 12c, 12d in the form of a rigid, tapered, elongate rod.

The rods extend so as to converge towards one another when the quadrants 13a-13d are connected together, and are each of the same length. The free ends of the rods terminate in close proximity to one another when the quadrants adopt the configuration visible in FIGS. 10a and 10b. In this configuration the free ends of the elements 12a, 12b, 12c, 12d constitute a composite probe 12.

When the handle is so configured the composite probe 12 defined by the free ends of the rods 12a, 12b, 12c, 12d may simultaneously contact a source of nucleic acid. This may be achieved through simple, manual grasping and manipulation of the handle 13 defined by the quadrants 13a-13d. The free ends of the probe elements 12a, 12b, 12c, 12d may include eg. pads or other projections that abut one another to define a composite tip in the form of an essentially continuous engagement surface for touching the nucleic acid.

The contact results in coating of the free ends approximately uniformly with the nucleic acid material. In order to promote adherence of nucleic acid to the free ends of the probe elements 12a-12d these may be made from, coated with or tipped with any of the materials discussed herein as being suitable for achieving this objective.

The probe/handle combination 12, 13 is supplied in the configuration shown in FIGS. 10a and 10b. A user grasps the handle 13 and uses this as a manipulator in order to contact the tip of the probe 12 defined by the free ends against or into nucleic acid-containing material, without any significant risk of the user's DNA contacting the probe elements. By reason of the choice of material of the free ends of the elements 12a-12d, and in accordance with the principles of the invention as described or defined herein, this results in approximately equal quantities of nucleic acid-bearing material adhering to each of the free ends.

The receptacles 11 optionally supported in a frame as described above may be supplied including, sealing the openings 14 therein, resiliently deformable bungs, peelable foil seals or similar seals that are removable to permit access to the interiors of the receptacles 11.

The receptacles 11 include retained inside them by virtue of the bungs or other seal types the reagents needed to effect a nucleic acid amplification reaction such as but not limited to the kinds discussed herein. Following contacting of the nucleic acid material by the free ends of the probes any retainer or detent securing the quadrants 13a-13d in their connected configuration is released as shown in FIG. 10c. As a result the quadrants, an individual example of which is visible in FIG. 10d, may be separated from one another to adopt the released configuration shown in FIGS. 10c and 10d.

This transfiguration may be effected through manual handling of the quadrants, without any need for the user to touch the probes. In consequence the chance of the user's DNA contacting the free ends is virtually zero.

When the quadrants 13a-13d adopt the separated configuration of FIGS. 10c and 10d the probe elements 12 are spaced from one another.

Thus in general terms the apparatus of FIG. 10 includes a plurality of probe elements to 12a-12d that are moveable one relative to another between contiguous and mutually spaced configurations, each probe element 12a, 12b, 12c, 12d including a tip part that when the probe elements adopt this contiguous configuration combines with the other tip parts to define a composite tip that is used for contacting nucleic acid-containing material.

The handle quadrants 13a-13d may then be used to manipulate the respective probe elements 12a-12d towards the openings 14 in the respective receptacles 11, following removal or opening of any seal of the general kind described above.

The probe elements 12a-12d may in this arrangement than be pushed via the respective openings 14a-14d into the inside of the receptacles.

At its end remote from the attached probe element each quadrant 13a-13d is formed including a tab 17 extending generally parallel to the direction of elongation of the quadrant. The tabs 17 may be used to facilitate fine manoeuvring by hand of the probe elements 12a-12d into the interior space defined in each receptacle 11.

Each of the probe elements 12a-12d is secured to its associated handle quadrant 13a-13d by way of a cylindrical sealing member 16 that depending on the precise construction of the probe element/handle combination is either formed integrally therewith or secured thereto eg. in the form of an annular collar.

Each of the openings 14 is circular in cross-section. The diameter of each sealing member 16 is such that on insertion of the attached probe element 12 inside one of the receptacles 11 the sealing member 16 firmly seals the receptacle against the ingress or egress of liquids, and in particular those containing or conveying nucleic acid. As a result the nucleic acid adhered to the probe element 12 in each case is presented to and placed in contact with the reagents therein. As a result nucleic acid amplification reactions eg. of the kinds discussed herein then take place.

Typically the receptacles 11 would be manufactured from transparent or translucent materials, or would include one or more transparent or translucent windows. As a result optical assessment of the reaction results could take place, for example using optical apparatuses. The frame 16 and/or the receptacles 11 therefore may be shaped and sized suitably for use with such apparatuses.

Referring now to FIGS. 11 to 16 another embodiment of nucleic acid sampling apparatus 21, 22, 23 according to the invention is shown in perspective view.

In FIG. 11 four receptacles 21a, 21b, 21c, 21d are formed as hollow frusta-conical members extending downwardly from the in-use underside of a rigid sheet 24 of polymeric material that is inert to (ie. has no effect on) nucleic acid. In the preferred embodiment of the invention the receptacles 21a-21d are formed by co-moulding them with the sheet 24.

The receptacles 21a-21d as illustrated are formed adjacent the four corners of a square sheet 24, although other numbers and patterns of receptacles 21 are possible within the scope of the invention; and the sheet 24 need not adopt the essentially square shape shown.

The receptacles 21a-21d may be supplied in a form that is initially sealed by way of a sealing membrane such as a foil that closes off openings 27a-27d formed at the in-use uppermost ends of the receptacles 21a-21d. The receptacles thus may be supplied pre-sealed and containing eg. PCR or other amplification reagents in a manner that assures the purity of such reagents until it is desired to use the apparatus. At such a time any foil present may be peeled off the sheet 24 in such a way as to open the holes for insertion therein of probe elements 22a, 22b, 22c, 22d described herein below.

The probe elements 22a-22d are formed as respective cones or conic sections of a material, such as one of those discussed herein, to which in accordance with the principles of the invention nucleic acid is adherent. In an alternative arrangement within the scope of the invention however the cones may be coated or tipped with such a material in order to provide for nucleic acid adherence to the parts of the apparatus at which it is required. Moreover other shapes than cones or parts thereof may be provided, although the sectioned cones shown are believed to be particularly suitable as probe elements.

The probe elements 22a-22d protrude from one side of a further sheet 28 of eg. polymeric material, especially a material that is "inert" to nucleic acid as explained above. Indeed, typically the sheet 28 would be made from the same material s the probe tips.

Sheet 28 is also essentially square, or may be shaped in a manner resembling a four-leafed clover such that a respective, essentially circular flange extends about the wider (upper) end of each of the cones defining the probe elements 22a-22d. The flanges 28 or other sheet formations adjacent the upper end of each probe element are joined one to another to define the sheet shape described.

As illustrated the four probe elements all extend from the same side of the sheet 28, in essentially the same direction when the sheet adopts an un-stressed configuration as shown in FIGS. 11 to 16.

On the side remote from the probe elements 22a-22d the sheet 28 as initially used is releasably secured to one end of an elongate manipulator 23.

Manipulator 23 is sized for grasping by hand and is formed primarily from a rigid material such as any of a wide range of plastic materials or metal alloys. The use of naturally occurring materials, or glass, as the primary constructional material of the manipulator 23 is not excluded, but these materials are thought not to be as convenient to form and handle as the plastics and metals mentioned.

Manipulator 23 includes an elongate, hollow cylindrical shank 30 that widens at one end to which sheet 28 is secured at a releasable attachment 31. At the opposite end shank 29 terminates in a gripping handle 32 that may adopt a range of possible forms.

In the illustrated embodiment the handle includes two parallel flat plates 32a, 32b that extend transversely to the elongate direction of shank 30 and are spaced from one another in this elongate direction by a reinforced stem member 32c.

The upper end of shank 30 includes on opposite sides thereof a pair of flanges 26a, 26b disposed on opposite sides of shank 30.

Each flange 26a, 26b defines an inwardly-facing, open-ended groove 26c, 26d. The respective grooves 26c, 26d oppose one another on opposite sides of shank 30, as shown in FIG. 11.

Extending from the in-use underside of plate 32a and rigidly secured thereto is an elongate plunger 29 that is a sliding fit inside the hollow interior of shank 30. Plunger 29 is moveable, through grasping of upper flat plate 32b, between a partly-exposed position as shown in FIG. 11 and a further position in which it is fully received inside the interior of shank 30.

In the latter position upper flat plate 32b may be rotated so as to cause the ends of parallel lower flat plate 32a to enter into the opposed grooves defined by the flanges 26a, 26b and thereby prevent plunger 29 from reverting to the partly-exposed position unless upper flat plate 32b is deliberately rotated to bring the ends of lower flat plate 32a clear of the aforesaid grooves.

The purpose of this arrangement is described below.

Sheet 28 is secured to the terminal periphery of attachment 31. Attachment 31 includes a hollow interior in which the in-use lower end of plunger 29 extends in a direction parallel to the direction of elongation of shank. Plunger 29 on movement between the partly-exposed and retracted positions described above acts as an activator for causing selective movement of the probe elements 22a-22d between a configuration in which their tips 33, remote from sheet 28, are in continuous contact; and a configuration as shown in FIGS. 11 to 16 in which the probe elements are spaced from one another by spacings corresponding to the spacings of the receptacles 21a-21d.

The plunger 29 achieves this effect by reason of the sheet 28 being flexible. The plunger 29 is in the initial condition of manipulator 23 secured to sheet 28. The rod is moveable inside the hollow shank 30 as described above. Movement of the rod towards the retracted position therefore draws the flexible sheet 28 partially inside the interior of attachment 31. This in turn draws the tip parts 33 towards one another so as to define a composite tip in which the tip parts are in contact with one another and define a single region for contacting nucleic acid-containing material.

Movement of the rod along the interior of the interior of shank 30 is normally effected by pulling on plate 32b, although it may also be achieved in a number of other ways.

Figure 17:
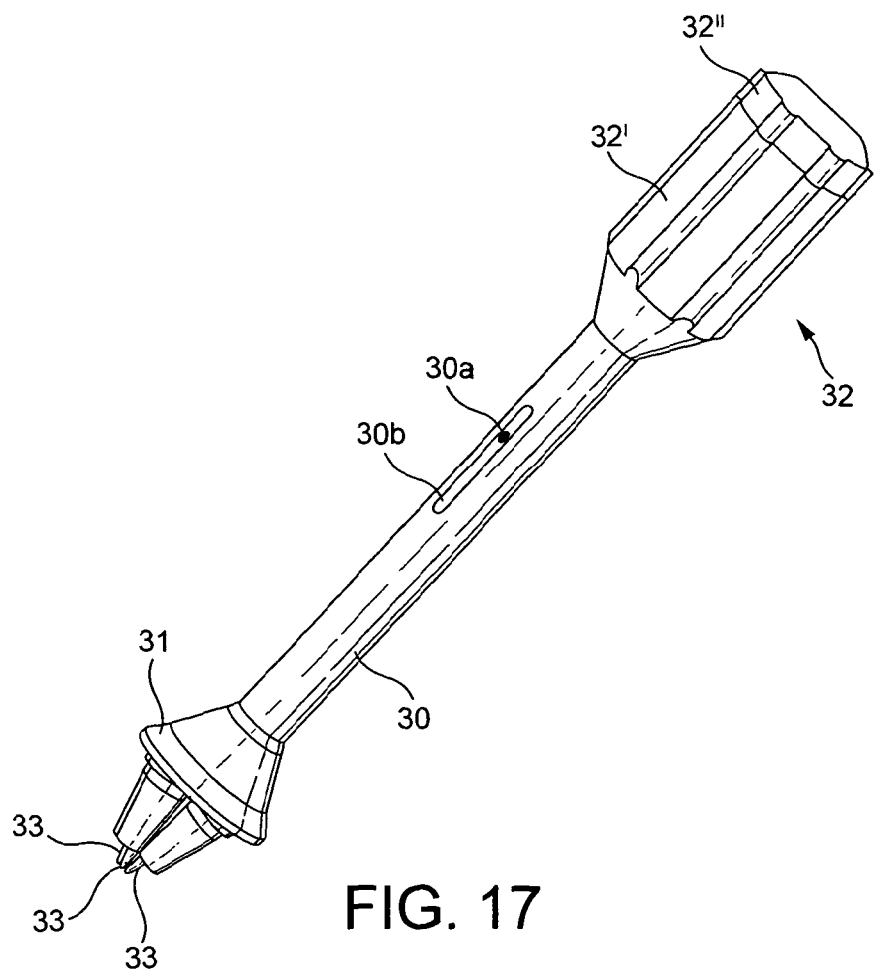
FIG. 17 shows in perspective view a variant on the arrangement of FIGS. 11 to 16.

For example a pin 30a as shown in FIG. 17 connected to the rod may be held slideably captive in a slot 30b so as to protrude on the exterior of shank 30. The user may move the rod by rotating cap 32" that is connected to the rod by an arrangement including a rotary-to-linear motion converting mechanism. The pin during movement of the rod slides along the slot which thereby defines readily detectable position end stops for the rod. The movement of the rod as described draws the sheet 28 into the interior of attachment 31 that in FIG. 17 is conical in shape.

In FIG. 17, which is a variant of the FIGS. 11 to 16 device, the handle 32 is essentially cylindrical in shape and formed in two parts 32' (joined to shank 30) and 32" (remote from shank 30). Handle part 32" is rotatable relative to part 32' and is connected to a locking mechanism inside handle 32 and shank 30. Rotation of part 32" relative to part 32' selectively activates a locking mechanism for the purpose of retaining the rod in its withdrawn position as exemplified by the position of pin 30a in slot 30b.

Regardless of the precise adjustment arrangement adopted however it is preferred that on releasing of the plunger 29 the resilience of the sheet causes the probe elements 22a-22d to revert to the un-stressed, mutually spaced apart arrangement illustrated in FIGS. 11 to 16, with the plunger 29 moving in the reverse direction inside the shank 30.

In addition to the foregoing, other types of locks, clips or detents of a releasable kind may be provided for the purpose of selectively retaining the probe elements 22a-22d in their contiguous configuration. Such locks, etc. typically would act to retain the plunger 29 in the position corresponding to the contiguous tip part arrangement described.

In its centre portion sheet 28 includes extending generally in the same direction, although for a lesser distance, as the probe elements a tamper-evident securing tag in the form of a circular "harpoon" element 34. The purpose and operation of this component are described herein below. Other forms of fastener for the probes, as will occur to the worker of skill in the art of receptacles, are within the scope of the invention.

The probe elements 22a-22d are capable of being broken away or otherwise released from manipulator 23. This may be achieved for example by reason of the union between the flanges and the remainder of sheet 28 being defined by frangible portions. In the preferred arrangement illustrated the entire sheet 28 may be retained temporarily captive on the manipulator 23 by reason of a clamping mechanism that is selectively releasable.

In use of the apparatus of FIG. 11 to 16 or 17 the plunger 29 initially is moved inside shank 30, through operation of an activator mechanism such as those described above, and locked (if a lock is present) in its position corresponding to drawing together of the tip parts as described above. Such movement of the plunger 29 may be upward or downward relative to shank 30, depending on the exact arrangement chosen. In the embodiment of FIG. 11 locking of the plunger is achieved by rotating the upper flat plate 32b to cause the edges of lower flat plate 32a to enter into the grooves 26c, 26d.

This movement of plunger 29 causes the tip parts 33a-33d of the probe elements 22a-22d to adopt their contiguous configuration so as to present essentially a single probe having a nucleic acid-contacting surface.

This surface may through manipulation using handle 32 be inserted into or rubbed against nucleic acid-containing material. In view of the materials from which at least the tip parts 33a-33d are made this results in adherence of nucleic acid, or material containing nucleic acid, essentially uniformly to the composite tip defined by the tip parts 33a-33d.

During this process and indeed subsequent operation of the apparatus an operator grasps the gripping handle 32. This permits the operator to avoid touching the probe elements, that are spaced from the handle 32 by the length of the shank 30.

Rubbing or other contacting of the nucleic acid-containing material by the composite tip results in approximately equal quantities of nucleic acid becoming adhered to each of the tip parts 33.

Once this has occurred the plunger 29 is released (eg. by releasing the lock or rotating the upper flat plate 32b as described). The resilience of sheet 28 causes the probe elements to adopt the un-stressed, mutually spaced configuration in which they may align with the openings 27a-27d in the receptacles 21a-21d. This motion occurs by reason of plunger 29 moving in the opposite direction to that giving rise to the contiguous configuration of the tips 33.

Following removal of any foil covering the receptacles 21 (preferably by peeling) the probe elements 22a-22d are inserted into the insides of the receptacles 21 such that the nucleic acid supported on the probe elements becomes exposed to the amplification reagents. The receptacles 21a-21d are transparent or translucent so that the results of the resulting reaction may be assessed using optical equipment.

The tapered shape of the probe elements 22a-22d may be chosen so that on insertion into the receptacles 21a-21d the probe elements 22a-22d seal the receptacles by reason of an interference fit with the top regions of the inner wall surfaces of the receptacles.

Of course other ways of sealing the receptacles, as will occur to the worker of skill in the art, lie within the scope of the invention. It is important primarily to ensure that an effective seal arises since the apparatus of the invention is expected to find use in eg. criminal legal cases, in which the integrity of evidential material is very important.

The sheet 24 in which the receptacles 21a-21d are moulded or otherwise formed optionally includes a central, through-going aperture. The purpose of this is to receive the (also optional) circular conical detent member 34 on or following insertion of the probe elements 22a-22d into the receptacles 21a-21d.

The detent member 34 extends predominantly on the same side of sheet 28 as the probe elements 22a-22d and includes sloping and undercut surfaces that allow it to become locked, in a snap-fitting manner, in the aperture in sheet 24 on such insertion of the probe elements 22a-22d into the receptacles.

The overall effect therefore of the detent member 34 and aperture is to provide for "tamper evident" securing of the probe elements in the receptacles 21a-21d. This feature is of particular benefit when the apparatus of the invention is required to act as evidence in eg. a criminal legal case, or a public enquiry into a disease outbreak.

As in the case of the FIG. 10a-10d embodiment of the invention, in the embodiment of FIGS. 11 to 16 the receptacles preferably are translucent or transparent in order to facilitate assessment of the amplification results without disturbing the conditions inside the receptacles. The materials of the insides of the receptacles are chosen to be inert to the reagents intended to be carried therein.

The embodiments of FIGS. 10 to 16 are all characterised by the feature of the probes in one way or another forming a seal on insertion into the optional receptacles. In consequence the probe elements may remain connected to the manipulator while the DNA amplification reactions occur.

In the embodiments described below the probe elements separate from the manipulator in the receptacles, and separate closures are used for sealing the latter.

Figure 18:
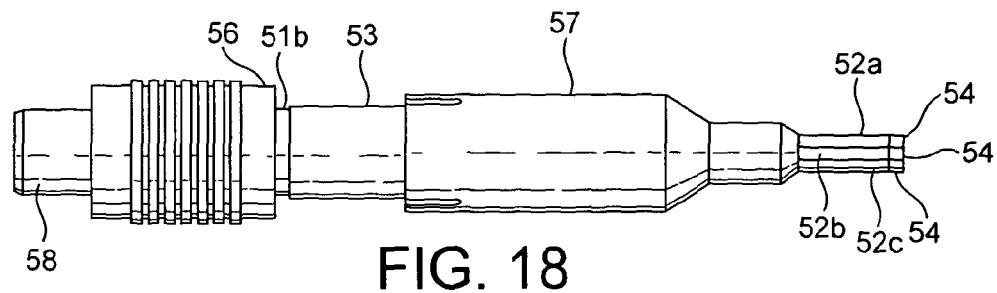
FIGS. 18 to 20 show in side elevational and cross-sectional views a further embodiment of the invention in which individual sampling probes may be ejected from a manipulator.
Figure 19:
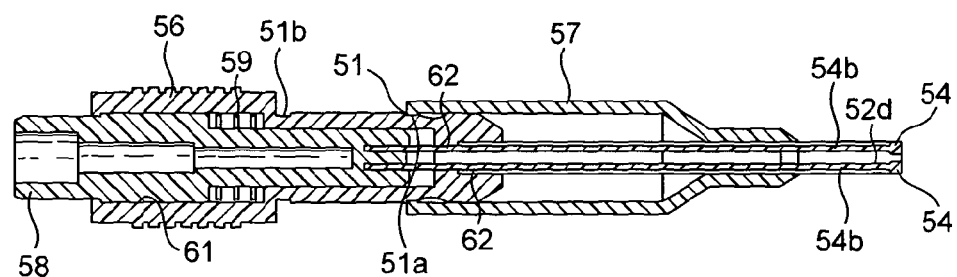
Figure 20:
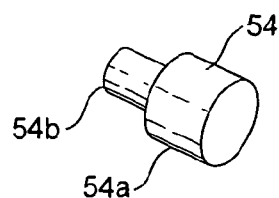

FIGS. 18 to 20 show in cross-sectional and side elevational view a further embodiment of the invention, that to some extent relies on probe elements having a degree of resilient deformability or "shape memory". This feature permits transfiguration of the probe elements between the convergent and mutually spaced arrangements that are characteristic of the embodiments described above.

In FIGS. 18 to 20 the probe elements 52a-52d are retained captive inside a manipulator in the form of an elongate housing 53. The probe elements adopt the form of elongate rods that are all of the same length. The rods may each be formed from so-called shape memory alloy materials and each include at a free end a removable tip part 54 made from one of the materials explained herein as being suitable for nucleic acid sampling. FIG. 20 shows one of the tip parts 54 in enlarged, perspective view.

At their ends remote from the tip parts the probe elements are secured together in a bundle, by reason of being clamped in the interior of a handle portion 56 of the housing 53.

A probe element activator in the form of hollow, cylindrical sheath portion 57 of housing 53 is retained slidably captive thereon so as to be moveable along the bundle of probe elements 52a-52d. In the as-supplied condition the sheath portion 57 overlies the probe elements 52a-52d over most of their length. At its end remote from tip parts 54 sheath portion 57 includes an annular, resiliently deformable detent in the form of ring 51 protruding inwardly into the interior of sheath part 57 from the cylindrical wall thereof. Ring 51 is selectively capable of being "snap-fitted" into respective forward 51*a* and rear 51*b* annular detent grooves formed in the outer surface of the part of handle portion 56 in which the rods are clamped. Sheath portion 57 is slideable along handle portion 56 to cause the ring 51 to engage either groove 51*a* or groove 51*b* as desired. This in turn causes releasable retention of sheath portion 57 in either of two positions on handle 56.

The probe elements 52*a*-52*d* are bent such that in their un-stressed condition their free ends supporting the tip parts 54 splay in order to provide for mutual spacing thereof. In this configuration the probe elements 52*a*-52*d* are suitable for insertion into receptacles such as the receptacles 21*a*-21*d* described above. The sheath portion 57 may be withdrawn along the housing 53 towards the handle portion 56 in order to achieve this condition.

Movement of the sheath portion 57 in the opposite direction towards the tip parts 54 so as to lie proximate them causes the bent parts of the probe elements 52*a*-52*d* to straighten. As a result the tip parts 54 converge against the resilient deformability of the probe elements to lie adjacent one another and define a composite tip that is suitable for engagement with nucleic acid-containing material.

The resulting composite tip may be caused so to engage such material through manual grasping of the handle portion 56. The sheath part may be operated manually as desired in order to move it between its withdrawn and proximate positions (with the above-described detent arrangement causing temporary retention of the sheath portion at one or other end of its range of movement) and hence convert the probe elements 52*a*-52*d* between the convergent and divergent arrangements.

The rods defining the probe elements 52*a*-52*d* are hollow and open-ended. As illustrated in FIG. 20 each tip part 54 is defined as a cylinder 54*a* of essentially the same outer diameter as one of the rods, with protruding from one end a cylindrical stud 54*b* of reduced diameter.

Each stud 54*b* is a friction fit into the open end of one of the rods. The friction retaining the tip parts relative to the rods may relatively easily be overcome by a pusher mechanism described below.

The pusher mechanism is defined in part by a cylindrical pushbutton 58 that protrudes from handle portion 56 at its end remote from the tip portions 54.

Pushbutton 58 is axially moveable under eg. thumb pressure against a restoring spring 59 in an elongate cylindrical bore 61 formed in the aforesaid end of handle portion 56.

Pushbutton 58 is rigidly connected inside housing 53 to four flexible pusher rods 62 that extend along the hollow interiors of the rods defining the probe elements 52*a*-52*d* to engage the studs 54*b* of the tip parts 54.

It will be apparent therefore that following withdrawal of sheath portion 57 to cause splaying of the tip parts 54, and following insertion of the tip parts 54 coated with nucleic acid into respective receptacles 21*a*-21*d*, operation of the pushbutton 58 causes ejection of the tip parts into the receptacles.

The receptacles may be closed eg. using closures such as but not limited to bungs, following withdrawal of the probe elements 52*a*-52*d*, with the result that the tip parts 54*a*-54*d* become separately sealed inside the receptacles in which PCR amplification then may occur.

Releasing of the pushbutton 58 causes withdrawal of the pusher rods such that fresh tip parts 54 may then be attached to the open ends of the probe elements 52*a*-52*d*, if necessary following cleaning. Alternatively the whole assembly may be disposable. Advancing of the sheath portion 57 to the position shown in eg. FIG. 18 causes the tip parts 54 to converge and again adopt their contiguous relationship shown, ready to perform further nucleic acid sampling operations.

Referring now to FIGS. 21-24 there is illustrated another variant of the apparatus.

Figure 21:
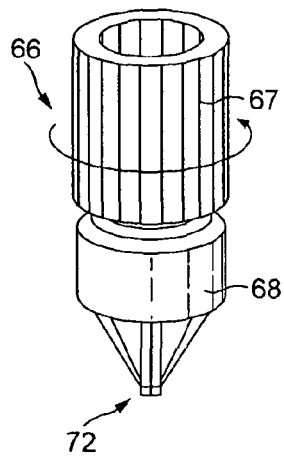
FIGS. 21 to 24 illustrate another arrangement, in which a mechanical cam arrangement may be used to cause spreading of initially contiguous tip parts before they are ejected from a manipulator.
Figure 22:
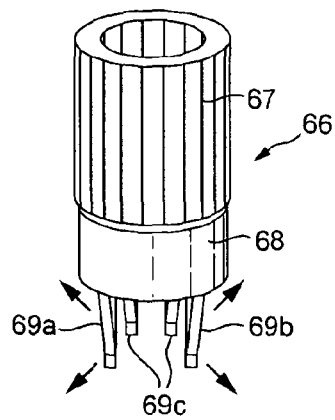
Figure 24:
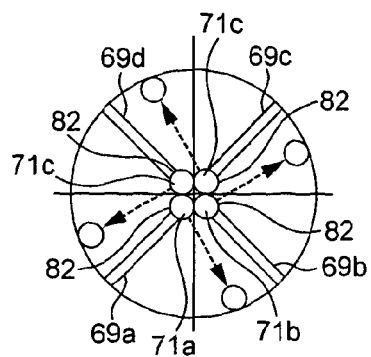

As best illustrated by FIGS. 21, 22 and 24 a handle 66 comprises in-use upper 67 and lower 68 cylindrical barrels that are of the same diameter as one another.

The lower barrel 68 has protruding from its free end an array of four moveable supports in the form of essentially triangular plates 69*a*-69*d*.

The barrels 67, 68 are rotatable relative to one another as signified by the arrow in FIG. 21 to cause the plates 69*a*-69*d* to move by way of a cam action described below. In this fashion the plates 69*a*-69*d* are moveable from an initial position, shown in FIG. 21, in which a plurality of tip portions 71*a*, 71*b*, 71*c*, 71*d* lie in a contiguous (nucleic acid-sampling) arrangement close to the longitudinal centre axis of the apparatus to a subsequent, tip-ejection position signified by dotted lines in FIG. 24 and shown in perspective view in FIG. 22. In the latter position the tip portions 71 all lie spaced from the centre axis and located for ejection into respective receptacles such as the receptacles 21 described below.

Figure 23:
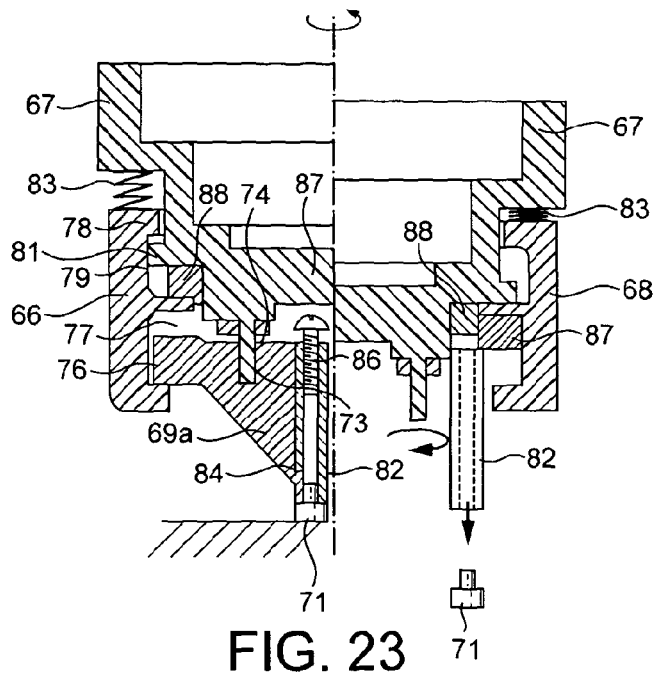

The plates 69*a*-69*d* are, as shown in FIG. 23 which is a sectional view showing parts of the device adopting respective operational positions in the two halves of the image, essentially right-angled triangular plates the hypoteneuses of which in the initial position of FIG. 21 converge to define a blunted point 72.

The triangular plates 69 each are pivotably suspended from above by way of a rotatable pivot pin 73. Each pivot pin 73 connects the underside of upper barrel 67 to the adjacent, non-hypoteneuse edge 74 of the plate 69 approximately halfway along its length.

The apex 76 of the plate 69 lying radially outwardly of pivot pin 73 is retained captive relative to lower barrel 68 by a spring 77. The upper and lower barrels 67, 68 are captive relative to one another and can move axially relative to one another against the action of (in practice, four) restoring springs 83 captured between the upper and lower barrels 67, 68 adjacent the outer periphery of the device. To accommodate axial movement of the barrels 67, 68 two retaining rings 78 and 79 formed inside and extending around the hollow interior of lower barrel 68 are axially spaced from one another and moveably trap between them an annular or part-annular flange formed on the exterior of part of upper barrel 67 received within lower barrel 68.

This arrangement is such that on rotation of the upper and lower barrels 67, 68 relative to one another each support (plate) 69 pivots about a vertical axis defined by its pivot pin 73.

This causes the vertically extending, non-hypoteneuse edge 82 of each plate 69 simultaneously to swing from the central, abutting position shown in FIGS. 21, 24 and the left-hand half of FIG. 23 to the ejection position, spaced from the device axis, shown in FIG. 22, and the right hand half of FIG. 23.

In the vicinity of each edge 82 each support 69 is hollow and defines an elongate bore 84 extending from the top of the support to the bottom.

A respective tip part 71 of essentially the same design as the tip parts 54 described above is retained captive at the lower end as shown of each bore 84 by reason of its stud being pushed into the bore.

A pushrod 86 having a domed cap 87 protrudes from the upper end of bore 84 and extends therealong to a height just above the end of the stud of tip part 54. The spacing between the lowermost end of pushrod 86 and the stud of tip part 54 is slightly less than the spacing between the underside of domed cap 87 and the edge 74 of each plate 69.

Movement of the plates 69 to the FIG. 22 positions swings each cap 87 of the pushrods 86 into alignment with a respective presser member 88 protruding downwardly from the underside of upper barrel 67.

Compression of the barrels 67, 68 together against the forces of the restoring springs 83 causes the presser members 88 to engage the caps 87. This drives the pushrods downwardly to engage the studs and thereby eject the tip parts 71 from the plates 69 respectively into the receptacles which may then be sealed eg. using bungs or other closures.

References

French D J, Howard R L, Gale N, Brown T, McDowell D G, Debenham P G. (2008) Interrogation of short tandem repeats using fluorescent probes and melting curve analysis: a step towards rapid DNA identity screening. *Forensic Sci Int Genet.* 4: 333-9.

Masaomi Iwasaki, Toshihiro Yonekawa, et al (2003) Validation of the Loop-Mediated Isothermal Amplification Method for Single Nucleotide Polymorphism Genotyping with Whole Blood. *Genome Letters*, Vol. 2, No. 3, 119-126.

3 Christophe Thibault, Childé rick Sé verac, Anne-Francüoise Mingotaud, Christophe Vieu, Monique Mauzac (2007) Poly(dimethylsiloxane) Contamination in Microcontact Printing and Its Influence on Patterning Oligonucleotides Langmuir, 23(21), 10706-10714.

The invention claimed is:

1. A nucleic acid sampling apparatus comprising a probe for supporting a nucleic acid sample; and a manipulator that is attachable to the probe such as to permit maneuvering of the probe, the probe being separable from the manipulator wherein the probe includes a plurality of probe elements wherein each probe element is moveable simultaneously relative to every other probe element between contiguous and mutually spaced configurations, each probe element including a tip part that when the probe elements adopt their contiguous configuration combines with the other tip parts to define a composite tip that is capable of contacting nucleic acid for the purpose of conveying a sample thereof.

2. An apparatus according to claim 1 wherein the composite tip when defined comprises a plurality of nucleic acid contacts secured respectively to and corresponding in number to the tip parts such that on contacting of nucleic acid by the composite tip each of the nucleic acid contacts engages generally the same amount of nucleic acid.

3. An apparatus according to claim 1 wherein the manipulator includes a probe element activator for causing selective movement of the probe elements between the contiguous and mutually spaced configurations.

4. An apparatus according to claim 2 wherein the manipulator includes an elongate shank; and the probe element activator is moveable along the shank to cause selective movement of the probe elements between the contiguous and mutually spaced configurations.

5. An apparatus according to claim 4 wherein the shank is hollow and the probe element activator substantially lies within and is moveable inside the interior of the shank.

6. An apparatus according to claim 5 wherein the shank includes a through-going aperture formed therein; and the probe element activator is contactable via the through-going aperture for the purpose of moving it inside the shank.

7. An apparatus according to claim 3 wherein the manipulator includes a rotatable member that is operatively connected to the probe element activator such that rotation of the rotatable member causes the probe element activator to move the probe elements between the continuous and mutually spaced configurations.

8. An apparatus according to claim 3 wherein each probe element includes a resiliently deformable, elongate member having a said tip part at one end; wherein the elongate members are arranged in a bundle extending alongside one another with their tip parts at the same end of the bundle; wherein each probe element is bent so that the tip parts tend to diverge from one another; and wherein the probe element activator includes a sheath part that encircles the bundle and is moveable along the elements of the bundle, the sheath part when proximate the tip parts causing the tip parts to converge in opposition to the resilient deformability of the probe elements to define the composite tip and the sheath part when spaced from the tip parts along the bundle permitting the tip parts to diverge from one another as a result of their bent shape and resilient deformability.

9. An apparatus according to claim 8 including one or more releasable detents for retaining the sheath part in a predetermined location.

10. An apparatus according to claim 3 including a resiliently deformable sheet supporting a plurality of the probe elements each defining a free end including a said tip part, wherein the sheet is transfigurable between a configuration in which the tip parts diverge from one another and a deformed configuration in which the probe elements are contiguous so that the tip parts define the composite tip.

11. An apparatus according to claim 1 further including a receptacle, including a sealable opening, for containing one or more reagents and a nucleic acid sample; operation of the manipulator causing or permitting insertion of the probe via the opening so as to locate the sample in the receptacle.

12. An apparatus according to claim 11 the probe of which includes a closure that on location of the sample in the receptacle closes the receptacle against egress or ingress of nucleic acid-containing material.

13. An apparatus according to claim 12 wherein the closure is or includes a liquid-proof sealing member that is secured to or integral with the probe.

14. An apparatus according to claim 12 including a closure that is secured to or integral with a plurality of the probes.

15. An apparatus according claim 11 wherein the closure and the manipulator selectively are separable from one another.

16. An apparatus according to claim 1 wherein the manipulator includes a source retaining a plurality of the probes in a manner isolating them from the ambient environment; and a dispensing mechanism for presenting the probes sequentially so as to expose at least a part of each for engagement with nucleic acid.

17. An apparatus according to claim 16 wherein the source is or includes a chamber containing one or more probes, the chamber including a chamber opening via which a said probe may protrude on operation of the dispensing mechanism.

18. An apparatus according to claim 17 wherein a protruding probe closes the chamber opening on dispensing.

19. An apparatus according to claim 1 wherein the manipulator includes one or more ejectors for ejecting at least one said probe element from the manipulator on its separation from the probe, the one or more ejectors being operable from a location, on the manipulator, that is remote from the probe element to be ejected.

20. An apparatus according to claim 19 including a plurality of the probe elements and a common ejector for ejecting more than one probe element from the manipulator.

21. An apparatus according to claim 19 including a plurality of the probe elements and a corresponding plurality of ejectors, a respective said ejector being operable to eject each said probe element.

22. An apparatus according to claim 1 wherein each probe element includes, or is configurable to define, a tip that is capable in use of contacting nucleic acid for the purpose of introducing a sample thereof into a receptacle on operation of the manipulator.

23. An apparatus according to claim 22 wherein at least the tip is made from or includes a polymeric material to which DNA or higher eukaryotic nucleic acid-containing material is adherent.

24. An apparatus according to claim 23 wherein the polymeric material is selected from the list comprising polycarbonate, glass, cyclic olefin copolymer such as Topas, acrylic such as PMMA, crystal polystyrene, polypropylene, HDPE, medium impact polystyrene, PVC, liquid crystal polymer 30%, trans ABS, acetal copolymer, polyester, polyetherimide, polyethylene, nylon, polyether polyurethane, styrene butadiene block copolymer, polypropylene, random copolymer, ethylene-vinyl acetate siloxane such as PDMS, and thermoplastic elastomer such as Santoprene.

25. The apparatus of claim 1 wherein the sampling device or part thereof to which the the nucleic acid containing material is adhered is treated to be DNA sterile, or the probe for supporting a said nucleic acid sample is treated so as to be DNA sterile.

\* \* \* \* \*